US012558129B2

(12) United States Patent
Zhang et al.

(10) Patent No.: US 12,558,129 B2
(45) Date of Patent: Feb. 24, 2026

(54) TRANSVERSE CONNECTING DEVICE AND REDUCTION AND FIXATION SYSTEM USING THE SAME

(71) Applicant: THE FOURTH MEDICAL CENTER OF THE GENERAL HOSPITAL OF THE CHINESE PEOPLE'S LIBERATION ARMY, Beijing (CN)

(72) Inventors: Wei Zhang, Beijing (CN); Zhongyang Liu, Beijing (CN); Jiantao Li, Beijing (CN); Hui Guo, Beijing (CN); Junsong Wang, Beijing (CN); Peifu Tang, Beijing (CN)

( * ) Notice: Subject to any disclaimer, the term of this patent is extended or adjusted under 35 U.S.C. 154(b) by 812 days.

(21) Appl. No.: 17/907,254

(22) PCT Filed: Sep. 2, 2022

(86) PCT No.: PCT/CN2022/116683
§ 371 (c)(1),
(2) Date: Sep. 23, 2022

(87) PCT Pub. No.: WO2023/245870
PCT Pub. Date: Dec. 28, 2023

(65) Prior Publication Data
US 2024/0216018 A1      Jul. 4, 2024

(30) Foreign Application Priority Data

Jun. 23, 2022    (CN) .......................... 202210718490.3
Jun. 23, 2022    (CN) .......................... 202210718502.2
(Continued)

(51) Int. Cl.
*A61B 17/70*        (2006.01)
*A61B 17/02*        (2006.01)
*A61B 17/88*        (2006.01)

(52) U.S. Cl.
CPC .......... *A61B 17/702* (2013.01); *A61B 17/025* (2013.01); *A61B 17/885* (2013.01); *A61B 2017/0256* (2013.01)

(58) Field of Classification Search
CPC .. A61B 17/7049–7052; A61B 17/7055; A61B 2017/8655
See application file for complete search history.

(56) References Cited

U.S. PATENT DOCUMENTS

2008/0109039 A1*  5/2008  Michielli ........... A61B 17/7049
                                                    606/246
2008/0177315 A1*  7/2008  Usher ................ A61B 17/7052
                                                    606/253
(Continued)

*Primary Examiner* — Eduardo C Robert
*Assistant Examiner* — Michelle C Green
(74) *Attorney, Agent, or Firm* — Novoclaims Patent Services LLC; Mei Lin Wong

(57) ABSTRACT

The present disclosure provides a transverse connecting device and a reduction and fixation system using the same. The transverse connecting device includes a connecting rod, wherein the connecting rod is provided with clamping heads, a lower end of each of the clamping heads is provided with two clamping arms, a clamping groove is formed between the two clamping arms, one of the two clamping arms is provided with a transverse through hole, the vertical through hole is internally threaded with a screw plug, a lower end of the screw plug abuts against a side of a first sliding block away from the clamping groove, when the screw plug is screwed into the vertical through hole, the screw plug pushes the first sliding block to slide into the clamping groove along the transverse through hole.

16 Claims, 28 Drawing Sheets

(30)　　　　Foreign Application Priority Data

Jun. 23, 2022　(CN) ......................... 202221587782.X
Jun. 23, 2022　(CN) ......................... 202221588589.8

(56)　　　　References Cited

U.S. PATENT DOCUMENTS

2012/0259369　A1 *　10/2012　Hammer ............ A61B 17/7052
　　　　　　　　　　　　　　　　　606/251
2017/0325849　A1 *　11/2017　Gleason ............. A61B 17/7052

* cited by examiner

TRANSVERSE CONNECTING DEVICE AND REDUCTION AND FIXATION SYSTEM USING THE SAME

This application claims priority to Chinese Patent Application No. CN202210718490.3 filed on Jun. 23, 2022 and titled "TRANSVERSE CONNECTING DEVICE AND REDUCTION AND FIXATION SYSTEM USING THE SAME", Chinese Patent Application No. CN202221587782.X filed on Jun. 23, 2022 and titled "TRANSVERSE CONNECTING DEVICE AND REDUCTION AND FIXATION SYSTEM USING THE SAME", Chinese Patent Application No. CN202210718502.2 filed on Jun. 23, 2022 and titled "TRANSVERSE CONNECTING DEVICE AND REDUCTION AND FIXATION SYSTEM USING THE SAME", and Chinese Patent Application No. CN202221588589.8 filed on Jun. 23, 2022 and titled "TRANSVERSE CONNECTING DEVICE AND REDUCTION AND FIXATION SYSTEM USING THE SAME", the entire contents of which are incorporated herein by reference.

TECHNICAL FIELD

The present disclosure relates to a medical instrument, and in particular to a transverse connecting device for a spine and a reduction and fixation system using the same.

BACKGROUND

For patients with lumbar vertebrae burst fracture, a fixation and reduction mechanism of a pedicle screw rod system is to reduce a fractured vertebral body by indirect traction. A surrounding of the fractured vertebral body can be effectively reduced due to the traction of annulus fibrosus of intervertebral discs, but a central piece of bone of an anterior middle column cannot be reduced by the traction, resulting in a collapse of a central part, and further resulting in insufficient reduction. At the same time, a cavity will be formed in a vertebral body after reduction, resulting in insufficient anterior support, and further leading to the long-term loss of a height of the vertebral body and even the degeneration of intervertebral discs in adjacent segments. Some patients even have aggravated kyphosis, residual low back pain, and even the failure of internal fixation.

There are two kinds of posterior short-segment fixation methods, namely, a cross-injured vertebra fixation and a combined injured vertebra fixation. The cross-injured vertebra fixation can further treat an injured vertebral body after reduction. If the reduction of the injured vertebral body is insufficient, internal reduction of the vertebral body can be performed through the pedicle channel, or bone grafting can be performed on the cavity in the vertebral body after reduction. However, through finite element analysis, biomechanics and clinical follow-up, scholars have found that the fixation of fractured vertebrae is not stable enough for burst fractures, and it is easy to fail. However, in short-segment fixation, combined with the plane pin of injured vertebra can increase the structural stability, avoid the quadrilateral effect and suspension effect of cross-segment fixation, disperse and reduce the internal fixation load, so it can effectively reduce the risk of internal fixation failure and secondary kyphosis, which is more in line with the biomechanical requirements of the spine.

The traditional fixation method of the injured vertebra is to place pins adjacent to the vertebral body and the injured vertebral body first, and then to reduce the vertebral body through a connecting rod. After the reduction, even if the injured vertebral body is poorly reduced or the anterior cavity is too large, the injured vertebral body is reduced and the bone grafting channel is occupied, so it is impossible to further operate in the injured vertebral body.

SUMMARY

The technical problem to be solved by the present disclosure is to provide a transverse connecting device and a reduction and fixation system using the same, which can realize the effective reduction of the fractured vertebral body and sufficient anterior support, and ensure the stability of the spine at the same time.

A transverse connecting device in the present disclosure, including: a connecting rod, wherein the connecting rod is provided with clamping heads, a lower end of each of the clamping heads is provided with two clamping arms, a clamping groove is formed between the two clamping arms, one of the two clamping arms is provided with a transverse through hole, the vertical through hole is internally threaded with a screw plug, a lower end of the screw plug abuts against a side of a first sliding block away from the clamping groove, when the screw plug is screwed into the vertical through hole, the screw plug pushes the first sliding block to slide into the clamping groove along the transverse through hole, the first sliding block is provided with a first clamping slot, a wall of the transverse through hole is provided with a first clamping block, and the first clamping block is located in the first clamping slot.

The transverse connecting device in the present disclosure, wherein two ends of the connecting rod are respectively provided with the clamping heads, the two clamping arms provided at the lower end of the clamping heads are respectively a first clamping arm and a second clamping arm, the clamping groove is formed between the first clamping arm and the second clamping arm, and the first clamping arm or the second clamping arm is provided with the transverse through hole.

The transverse connecting device in the present disclosure, wherein one end of the connecting rod is provided with the clamping heads, the two clamping arms provided at the lower end of the clamping heads are respectively a first clamping arm and a second clamping arm, the clamping groove is formed between the first clamping arm and the second clamping arm, the first clamping arm is located between the connecting rod and the second clamping arm, and the first clamping arm is provided with the transverse through hole.

A reduction and fixation system using the above-mentioned transverse connecting device in the present disclosure, including: a vertebral body distraction support pin, an upper pedicle screw and a lower pedicle screw, wherein the vertebral body distraction support pin is installed on a fractured vertebral body, the upper pedicle screw and the lower pedicle screw are respectively installed on an upper vertebral body and a lower vertebral body of the fractured vertebral body, a fixing rod is connected between the upper pedicle screw and the lower pedicle screw, the clamping heads of the transverse connecting device clamp the fixing rod through the clamping groove, and the connecting rod of the transverse connecting device is fixedly connected to the vertebral body distraction support pin.

The reduction and fixation system in the present disclosure, wherein a supporting block is fixedly connected to the vertebral body distraction support pin, the supporting block is provided with an installation groove, the connecting rod of the transverse connection device is inserted into the installation groove, a screw is screwed between two groove walls of the installation groove, the screw abuts against the connecting rod of the transverse connecting device, and the screw fixes the connecting rod in the installation groove.

The reduction and fixation system in the present disclosure, wherein a supporting block is fixedly connected to the vertebral body distraction support pin, the supporting block is provided with a first through hole, the hole wall of the first through hole is provided with a second through hole, the connecting rod of the transverse connecting device is inserted into the first through hole, the second through hole is threaded with a screw, and the screw abuts against the connecting rod of the transverse connecting device.

The reduction and fixation system in the present disclosure, wherein the vertebral body distraction support pin includes a pin body and a pin cap, the pin body includes an inner core, an outer sleeve and an expansion balloon, the inner core is screwed into the outer sleeve, an upper end and a lower end of the inner core extend out of the outer sleeve, the lower end of the inner core is provided with a tapered pin head, the expansion balloon is sleeved on the inner core between the tapered pin head and the lower end of the outer sleeve, the pin cap includes an upper pin cap and a pressurizing cap, the upper pin cap has a cylindrical structure, a lower end of a barrel cavity of the upper pin cap is connected to an upper end of the outer sleeve, an upper end of the inner core extends to an upper end of the barrel cavity of the upper pin cap, and the upper end of the inner core is clamped and slidably connected with the pressurizing cap, the pressurizing cap is clamped and slidably connected with the upper pin cap and can slide along the axial direction of the inner core and the upper pin cap, when the pressurizing cap slides upward along the axial direction of the upper pin cap to release a clamping sliding connection with the upper pin cap, the pressurizing cap still keeps the clamping sliding connection with the inner core, when the tapered pin head moves near the lower end of the outer sleeve, the expansion balloon expands, the tapered pin head and the expansion balloon in an expanding state are both located in the fractured vertebral body, the supporting block is fixedly connected to an outer wall of the outer sleeve, and the supporting block is located outside the fractured vertebral body.

The reduction and fixation system in the present disclosure, wherein the expansion balloon includes an upper collar and a lower collar, both of which are sleeved on the inner core between the tapered pin head and the lower end of the outer sleeve, the upper collar abuts against the lower end of the outer sleeve, the lower collar abuts against the upper end of the tapered pin head, a plurality of expansion pieces are fixedly connected between the upper collar and the lower collar, the expansion pieces are circumferentially arranged along the inner core, when the tapered pin head moves close to the lower end of the outer sleeve, the expansion pieces can bulge and deform away from the inner core, the upper pin cap is fixedly connected with two first lugs, and the pressurizing cap is fixedly connected with two second lugs.

The reduction and fixation system in the present disclosure, wherein the upper pin cap includes an upper barrel and a lower barrel which are integrally formed, an inner barrel diameter of the upper barrel is larger than an inner barrel diameter of the lower barrel, the upper end of the outer sleeve has a hollow prism structure, a lower part of a barrel cavity of the lower barrel has a prism shape matched with the upper end of the outer sleeve, an upper part of the barrel cavity of the lower barrel is provided with a first clamping table, the lower part of the barrel cavity of the lower barrel is sleeved on the upper end of the outer sleeve, the upper end of the outer sleeve abuts against the first clamping table, and the upper end of the inner core passes through the barrel cavity of the lower barrel and extends into the barrel cavity of the upper barrel.

The reduction and fixation system in the present disclosure, wherein the outer wall of the outer sleeve is provided with a second clamping table, and the lower end of the lower barrel abuts against the second clamping table.

The reduction and fixation system in the present disclosure, wherein the upper end of the inner core has a prismatic structure, the pressurizing cap has a cylindrical structure, the barrel cavity of the pressurizing cap has a prismatic shape matching with the upper end of the inner core, the pressurizing cap is sleeved on the upper end of the inner core, the outer wall of the pressurizing cap is fixedly provided with a second clamping block, the inner wall of the upper barrel is provided with a second clamping slot axially arranged, the second clamping block is positioned in the second clamping slot and can slide along the second clamping slot, when the pressurizing cap slides upward along the axial direction of the upper pin cap to make the second clamping block separate from the second clamping slot, and the pressurizing cap is still sleeved on the upper end of the inner core.

When the present disclosure is used, the upper pedicle screw and the lower pedicle screw are respectively installed on the upper vertebral body and the lower vertebral body of the fractured vertebral body, the vertebral body distraction support pin is installed on the fractured vertebral body, and then the clamping head of the transverse connecting device clamps the fixing rod through the clamping groove, and the connecting rod of the transverse connecting device is fixedly connected to the vertebral body distraction support pin. In this way, the inside of the fractured vertebral body is propped up by the vertebral body distraction support pins, that is, the collapsed bone pieces of the fractured vertebral body are propped up, then the fractured vertebral body is pulled and reduced by the upper pedicle screw, the lower pedicle screw and the fixing rod, and finally the vertebral body distraction support pins, the fixing rod, the upper pedicle screw and the lower pedicle screw are fixedly connected together by the transverse connecting device, thereby realizing the effective reduction of the fractured vertebral body and sufficient anterior support, and ensuring the stability of the spine.

The present disclosure will be further described below with reference to the accompanying drawings.

DETAILED DESCRIPTION OF THE EMBODIMENTS

Figure 1:
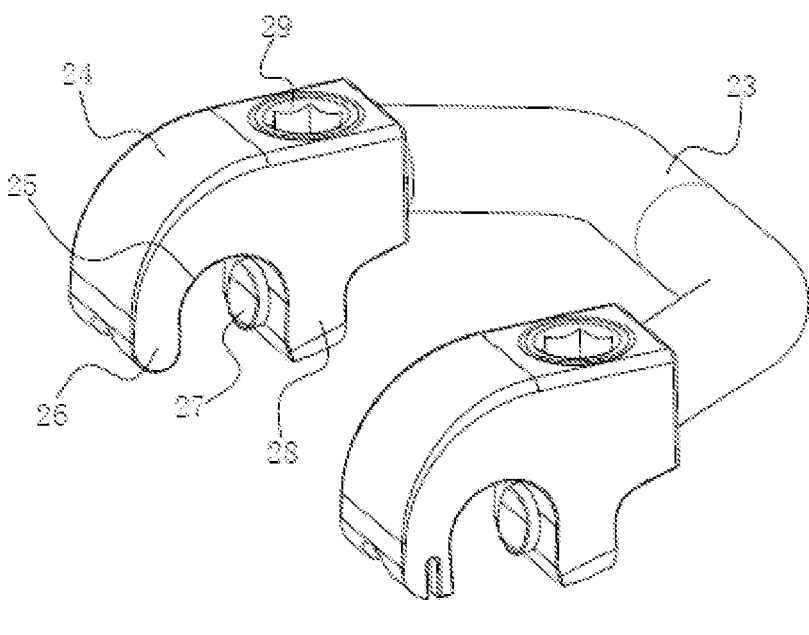
FIG. 1 is a structural schematic diagram showing a transverse connecting device according to an embodiment of the present disclosure.
Figure 2:
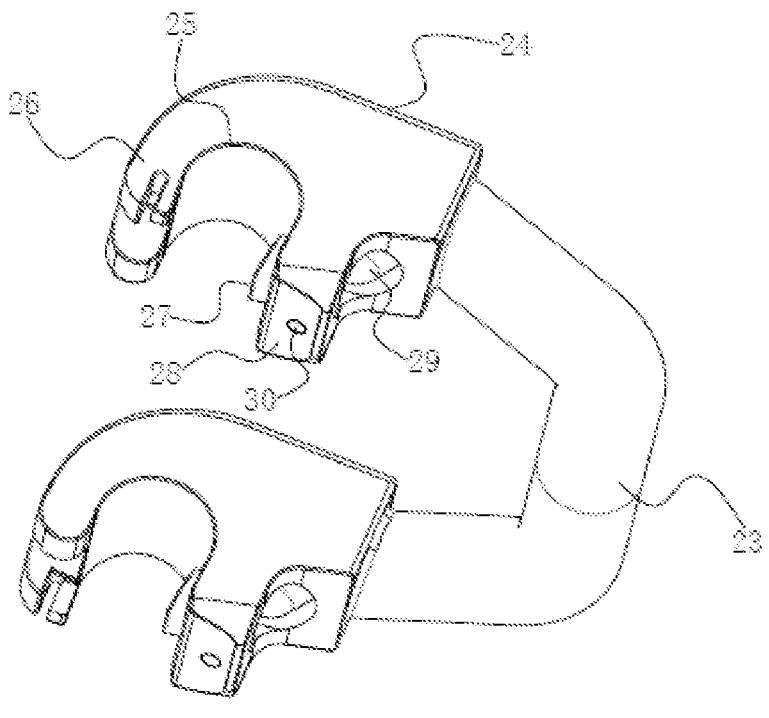
FIG. 2 is the structural schematic diagram showing a transverse connecting device according to an embodiment of the present disclosure.

In order to make the above objects, features and advantages of the present disclosure more obvious and understandable, the specific embodiments of the present disclosure will be described in detail below with reference to the accompanying drawings.

The directions or positional relationships indicated by the terms "up", "down", "front", "back", "left" and "right" appearing in the embodiments of the present disclosure are based on the orientation or positional relationship shown in the drawings, only for the convenience of describing the present disclosure and simplifying the description, instead of indicating or implying that the referred device must have a specific orientation, be constructed and operated in a specific orientation, and therefore cannot be In the description of the present disclosure, it should be noted that unless otherwise specified and limited, the terms "set", "installed", "connected" and "connected" should be understood broadly, for example, they can be fixedly connected, detachably connected, or integrally connected; May be mechanically connected; Can be directly connected or indirectly connected through an intermediate medium; For those of ordinary skill in the art, the specific meanings of the above terms in the present disclosure can be understood in specific situations.

If there are descriptions related to "first" and "second" in the embodiments of the present disclosure, the descriptions of "first" and "second" are only used for descriptive purposes, and cannot be understood as indicating or implying their relative importance or implicitly indicating the number of indicated technical features.

First Embodiment

As shown in FIG. 1 and in combination with FIG. 2 to FIG. 18, a transverse connecting device in the present disclosure includes a connecting rod 23, wherein the connecting rod 23 is provided with clamping heads 24, specifically, the clamping heads 24 are respectively arranged at both ends of the connecting rod 23. A lower end of each clamping head 24 is provided with two clamping arms, a clamping groove 25 is formed between the two clamping arms, and one of the two clamping arms is provided with a transverse through hole 32. Specifically, the two clamping arms at the lower end of the clamping head 24 are a first clamping arm 28 and a second clamping arm 26, respectively; the clamping groove 25 is formed between the first clamping arm 28 and the second clamping arm 26, and the first clamping arm 28 or the second clamping arm 26 is provided with the transverse through hole 32. A first sliding block 27 is arranged in the transverse through hole 32, and the clamping head 24 is provided with a vertical through hole 31 communicating with the transverse through hole 32. The vertical through hole 31 is internally threaded with a screw plug 29, and a lower end of the screw plug 29 abuts against a side of the first sliding block 27 away from the clamping groove 25. When the screw plug 29 is screwed into the vertical through hole 31, the screw plug 29 pushes the first sliding block 27 to slide into the clamping groove 25 along the transverse through hole 32. The first sliding block 27 is provided with a first clamping slot 36, and a wall of the transverse through hole 32 is provided with a first clamping block 30, and the first clamping block 30 is located in the first clamping slot 36.

The connecting rod 23 is U-shaped, and two clamping heads 24 are fixedly connected to both ends of the connecting rod 23, respectively. For each clamping head 24, the first clamping arm 28 is arranged near an end of the connecting rod 23, while the second clamping arm 26 is arranged far away from the end of the connecting rod 23. In the embodiment of the present disclosure, the first clamping arm 28 is provided with the transverse through hole 32.

Figure 15:
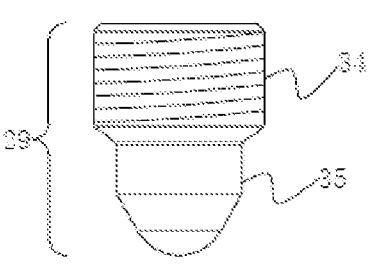
FIG. 15 is a front view showing a screw plug according to an embodiment of the present disclosure.
Figure 16:
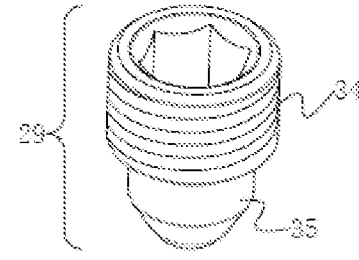
FIG. 16 is a perspective view showing a screw plug according to an embodiment of the present disclosure.

As shown in FIG. 15 and FIG. 16, the screw plug 29 is cylindrical, and the screw plug 29 is coaxially arranged with the vertical through hole 31. A diameter of an upper half 34 of the screw plug 29 is larger than that of a lower half 35 of the screw plug 29, and an outer side wall of the upper half 34 of the screw plug 29 is provided with a polygonal countersink. One end of a rotary tool is inserted into the polygonal countersink, and then the screw plug 29 can be screwed into the vertical through hole 31 or out of the vertical through hole 31 by rotating the rotary tool. A lower end of the lower half 35 of the screw plug 29 is a circular arc convex surface.

Figure 3:
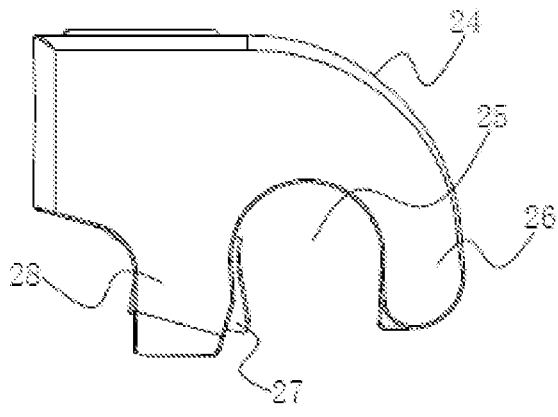
FIG. 3 is a front view showing a clamping head according to an embodiment of the present disclosure.
Figure 4:
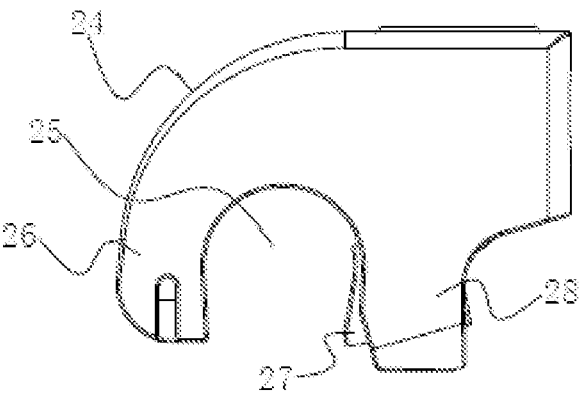
FIG. 4 is a rear view showing a clamping head according to an embodiment of the present disclosure.
Figure 5:
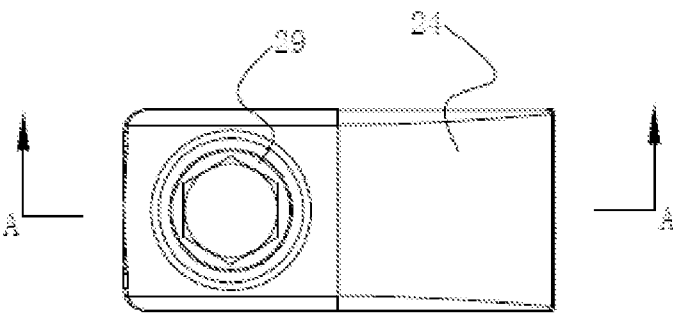
FIG. 5 is a top view showing a clamping head according to an embodiment of the present disclosure.
Figure 17:
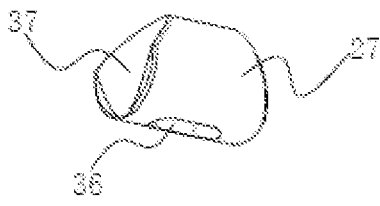
FIG. 17 is a perspective view showing a first sliding block according to an embodiment of the present disclosure.
Figure 18:
FIG. 18 is a perspective view showing a first sliding block according to an embodiment of the present disclosure.

As shown in FIG. 3 and FIG. 4, the clamping groove 25 has an arc shape. As shown in FIG. 17 and FIG. 18, the first sliding block 27 has a cylindrical shape, and is coaxially arranged with the transverse through hole 32. One end face 37 of the first sliding block 27 is arranged away from the clamping groove 25, and the other end face 38 of the first sliding block 27 is arranged close to the clamping groove 25. The end face 37 of the first sliding block 27 away from the clamping groove 25 is a side face of the first sliding block 27 away from the clamping groove 25. The end surface 37 of the first sliding block 27 away from the clamping groove 25 is an arc concave surface, so as to match with the lower end of the lower half 35 of the screw plug 29. The end surface 38 of the first sliding block 27 near the clamping groove 25 is also an arc concave surface, so as to match with the shape of the clamping groove 25. An outer circumferential wall of the first sliding block 27 is provided with a first clamping slot 36, the first clamping slot 36 has a strip shape, and the first clamping slot 36 is arranged along an axial direction of the first sliding block 27.

Figure 6:
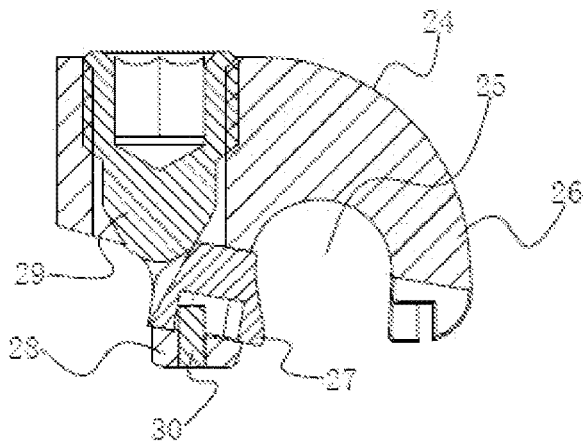
FIG. 6 is a sectional view along line A-A in FIG. 5.
Figure 7:
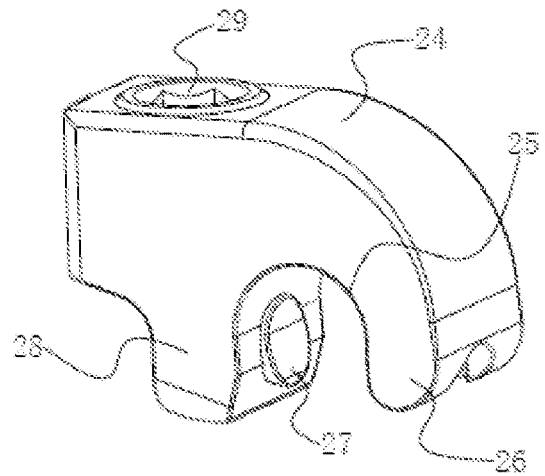
FIG. 7 is a perspective view showing a clamping head according to an embodiment of the present disclosure.
Figure 8:
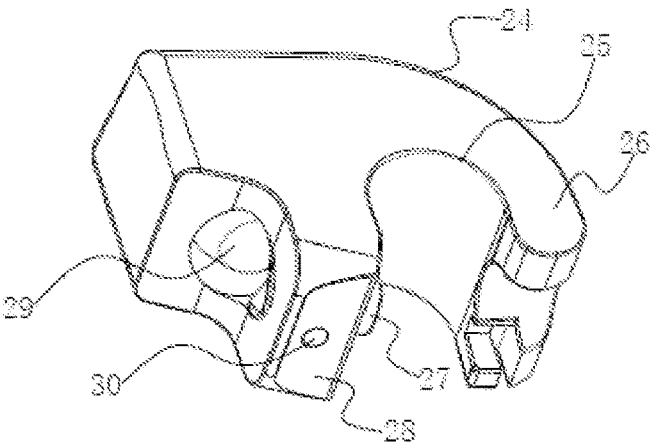
FIG. 8 is a perspective view showing a clamping head according to an embodiment of the present disclosure.
Figure 9:
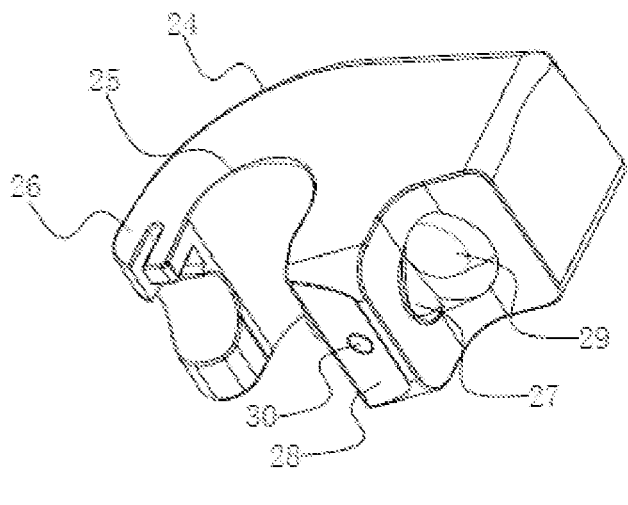
FIG. 9 is a perspective view showing a clamping head according to an embodiment of the present disclosure.
Figure 10:
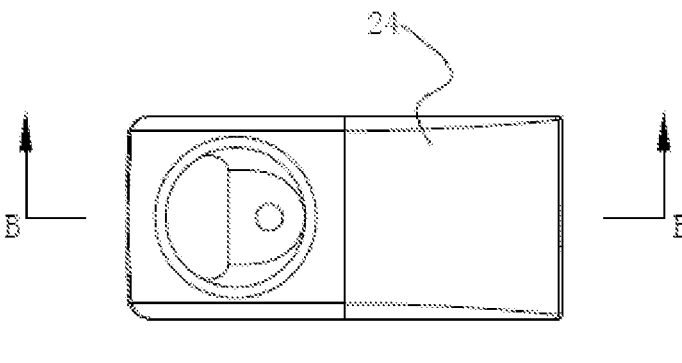
FIG. 10 is a top view showing a clamping head (hiding a screw plug, a first sliding block and a first clamping block) according to an embodiment of the present disclosure.
Figure 11:
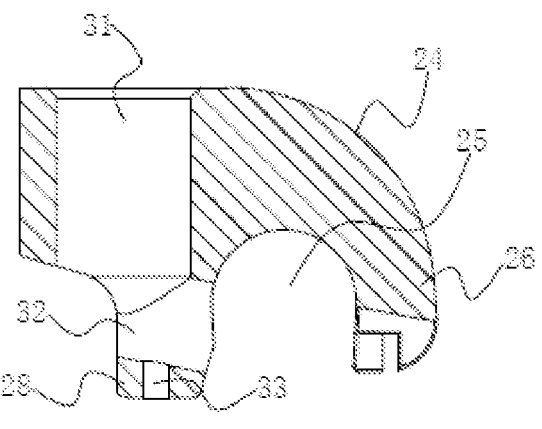
FIG. 11 is a sectional view along line B-B in FIG. 10.
Figure 12:
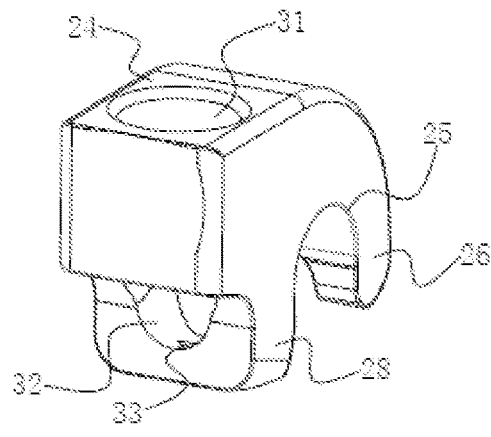
FIG. 12 is a perspective view showing a clamping head (hiding a screw plug, a first sliding block and a first clamping block) according to an embodiment of the present disclosure.
Figure 13:
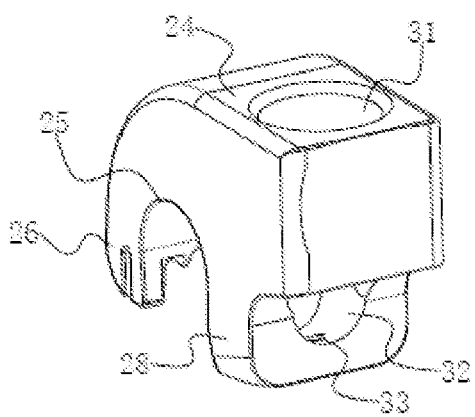
FIG. 13 is a perspective view showing a clamping head (hiding a screw plug, a first sliding block and a first clamping block) according to an embodiment of the present disclosure.
Figure 14:
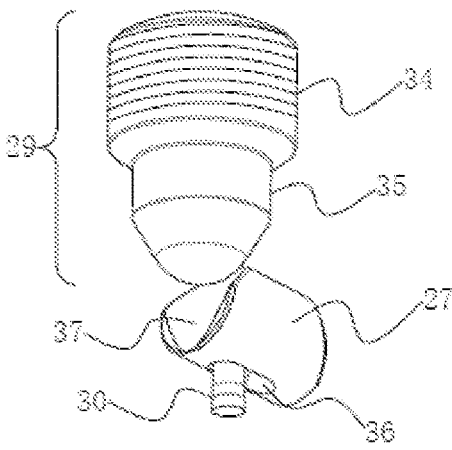
FIG. 14 is a diagram showing a relative positional relationship among a screw plug, a first sliding block and a first clamping block according to an embodiment of the present disclosure.

As shown in FIG. 6 and in combination with FIG. 11 and FIG. 14, the first clamping block 30 is cylindrical, and a lower end of the first clamping arm 28 is provided with a mounting hole 33, which communicates with the transverse through hole 32. The first clamping block 30 is fixedly arranged in the mounting hole 33, an upper end of the first clamping block 30 extends into the transverse through hole 32, and the upper end of the first clamping block 30 is located in the first clamping slot 36 of the first sliding block 27.

When the screw plug 29 is screwed into the vertical through hole 31, the lower end of the lower half 35 of the screw plug 29 abuts against the end surface 37 of the first sliding block 27 away from the clamping groove 25. As the screw plug 29 continues to be screwed in, the screw plug 29 pushes the first sliding block 27 to slide along the transverse through hole 32 to the clamping groove 25, and when sliding to a certain position, the first sliding block 27 stops sliding due to the blocking effect of the first clamping block 30. After the screw plug 29 is screwed out of the vertical through hole 31, the first sliding block 27 can be pushed to slide away from the clamping groove 25 along the transverse through hole 32; and when sliding to a certain position, the first sliding block 27 will no longer slide due to the blocking effect of the first clamping block 30.

Figure 54:
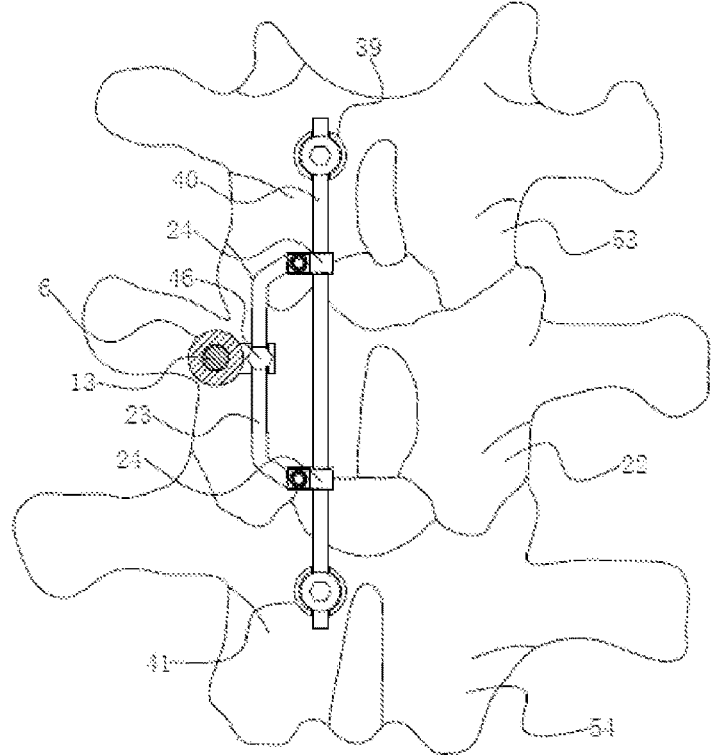
FIG. 54 is a diagram showing a use state of a reduction and fixation system according to an embodiment of the present disclosure.
Figure 55:
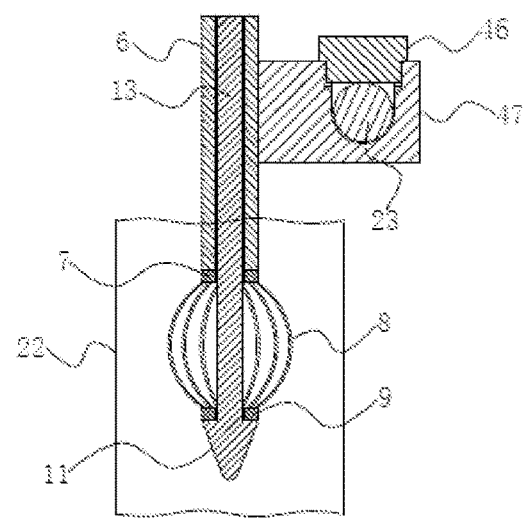
FIG. 55 is a diagram showing a connection state of a supporting block and a connecting rod according to an embodiment of the present disclosure.
Figure 56:
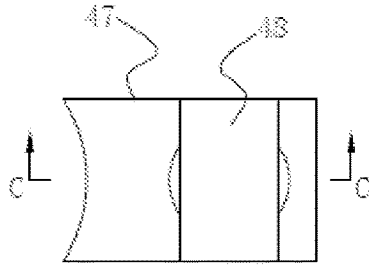
FIG. 56 is a top view showing a supporting block according to an embodiment of the present disclosure.
Figure 57:
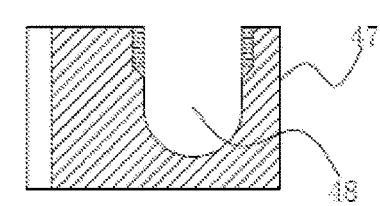
FIG. 57 is a sectional view along line C-C in FIG. 56.
Figure 58:
FIG. 58 is a structural schematic diagram showing a screw according to an embodiment of the present disclosure.

As shown in FIG. 54, a reduction and fixation system using the above-mentioned transverse connecting device in the present disclosure includes a vertebral body distraction support pin, an upper pedicle screw 39 and a lower pedicle screw 41, wherein the vertebral body distraction support pin is installed on a fractured vertebral body 22, and the upper pedicle screw 39 and the lower pedicle screw 41 are respectively installed on an upper vertebral body 53 and a lower vertebral body 54 of the fractured vertebral body 22, a fixing rod 40 is connected between the upper pedicle screw 39 and the lower pedicle screw 41, the clamping heads 24 of the transverse connecting device clamp the fixing rod 40 through the clamping groove 25, and the connecting rod 23 of the transverse connecting device is fixedly connected to the vertebral body distraction support pin.

The two clamping heads 24 of the transverse connecting device clamp the fixing rod 40 through their own clamping grooves 25, and the two clamping heads 24 are located above and below the vertebral body distraction support pin, respectively.

Figure 19:
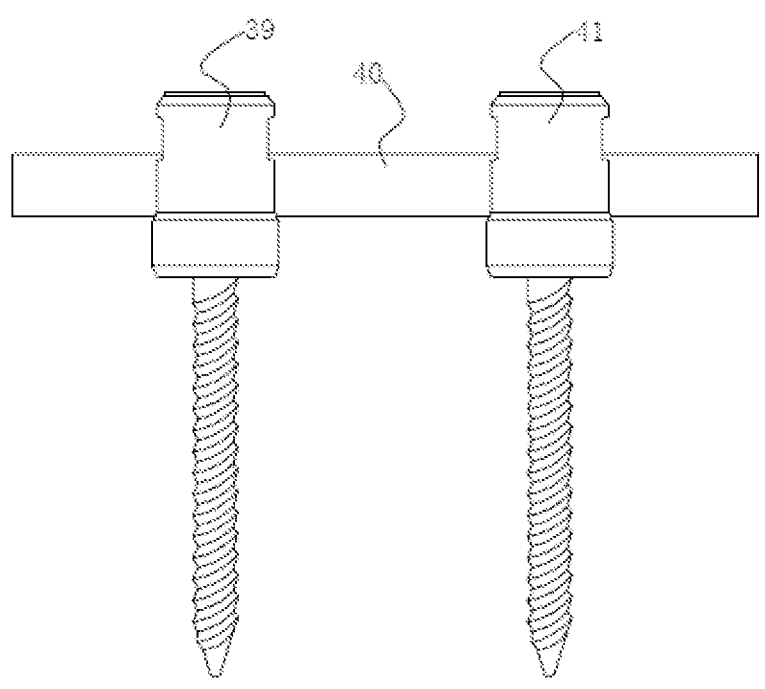
FIG. 19 is a diagram showing a relative positional relationship among an upper pedicle screw, a lower pedicle screw and a fixing rod according to an embodiment of the present disclosure.
Figure 20:
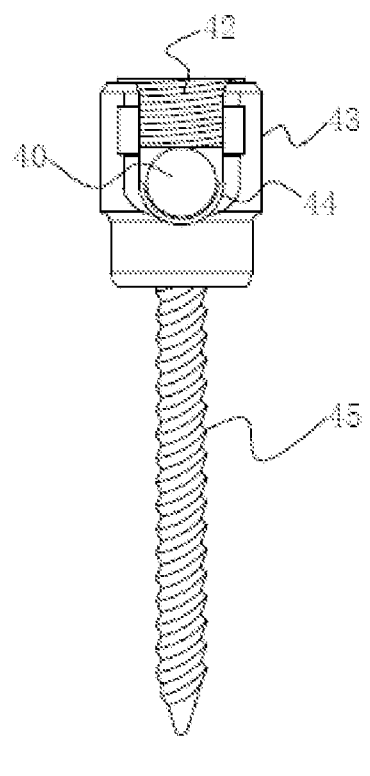
FIG. 20 is a front view showing an upper pedicle screw (and also a front view showing a lower pedicle screw) according to an embodiment of the present disclosure.
Figure 21:
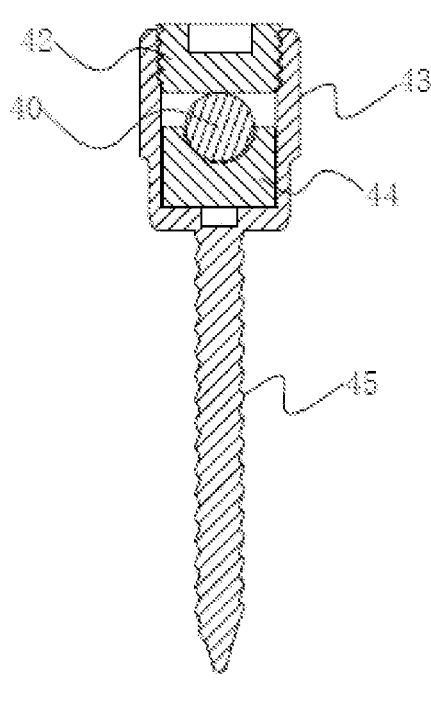
FIG. 21 is a front sectional view showing an upper pedicle screw (and also a front sectional view showing a lower pedicle screw) according to an embodiment of the present disclosure.

As shown in FIG. 19 and in combination with FIG. 20 and FIG. 21, the upper pedicle screw 39 and the lower pedicle screw 41 have the same structure, and both of which include a barrel-shaped screw seat 43, a bottom wall of the screw seat 43 is provided with a screw rod 45, a side wall of the screw seat 43 is provided with a U-shaped notch for accommodating the fixing rod 40, and an inner cavity of the screw seat 43 is provided with a cushion block 44 and a fixing plug 42, the cushion block 44 is located below the fixing plug 42, which is screwed into the screw seat 43, and the fixing rod 40 is located between the fixing plug 42 and the cushion block 44. When the fixing plug 42 is screwed into the screw seat 43, the fixing plug 42 can clamp the fixing rod 40 with the cushion block 44, thereby fixedly connecting the fixing rod 40 with the upper pedicle screw 39 and the lower pedicle screw 41.

Figure 22:
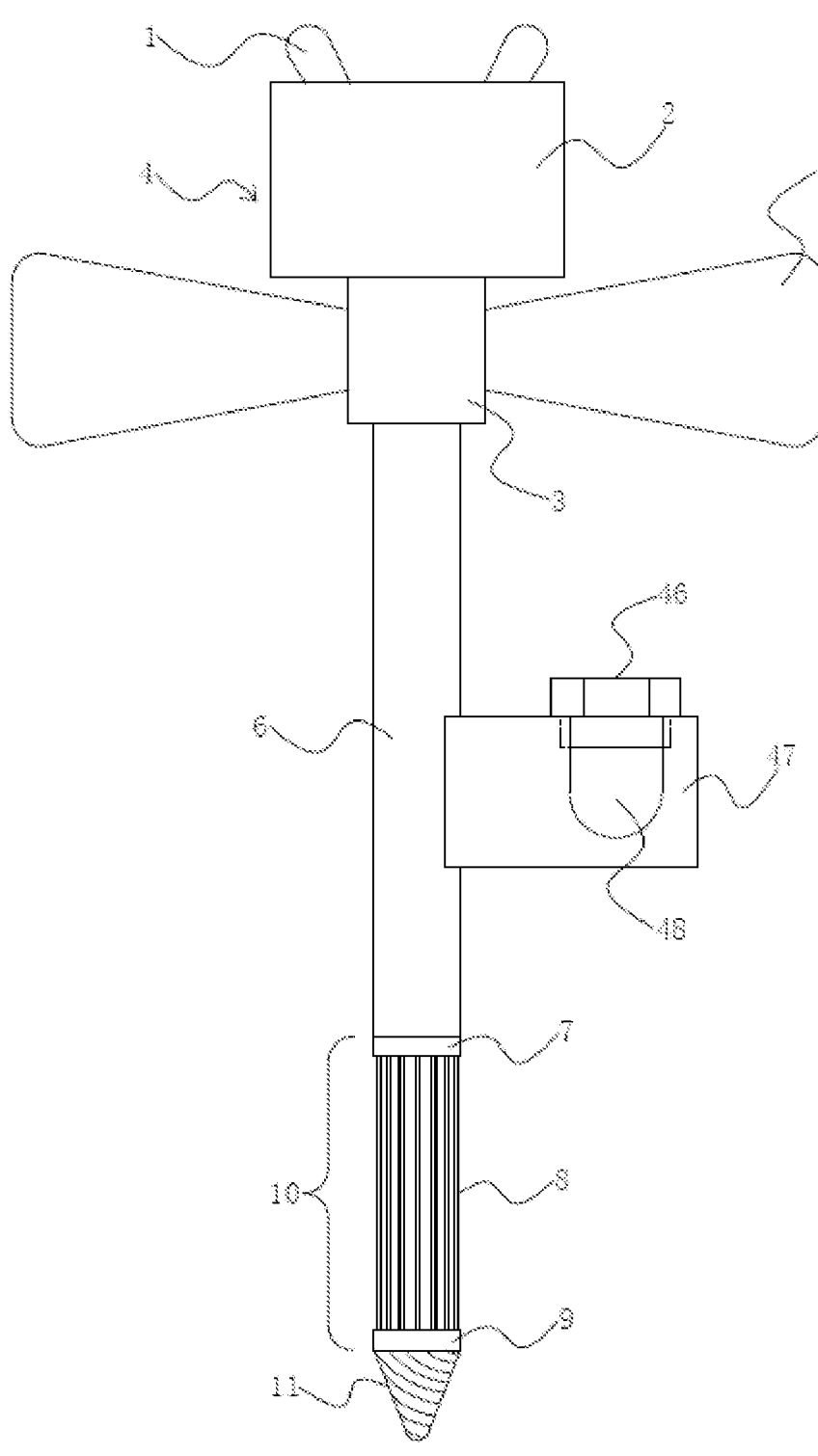
FIG. 22 is a front view showing a vertebral body distraction support pin according to an embodiment of the present disclosure.

As shown in FIG. 22 and in combination with FIG. 23, FIG. 50, FIG. 51 and FIG. 54 to FIG. 58, in the reduction and fixation system of the present disclosure, a supporting block 47 is fixedly connected to the vertebral body distraction support pin, an installation groove 48 is provided on the supporting block 47, and the connecting rod 23 of the transverse connection device is inserted into the installation groove 48. A screw 46 is screwed between two groove walls of the installation groove 48, the screw 46 abuts against connecting rod 23 of the transverse connecting device, and the screw 46 fixes the connecting rod 23 in the installation groove 48.

When installing the transverse connection device, the clamping grooves 25 of the two clamping heads 24 are clamped on the fixing rod 40, and then the connecting rod 23 is placed in the installation groove 48 of the supporting block 47. The screw plug 29 of each clamping head 24 is screwed into the respective vertical through hole 31, so that the clamping head 24 clamps the fixing rod 40 through respective clamping groove 25 thereof, and then the screw 46 is screwed into the installation groove 48 until the screw 46 abuts against the connecting rod 23, the connecting rod 23 and the supporting block 47 are fixedly connected by the screw 46, and at the same time, the vertebral body distraction support pin, the fixing rod 40, the upper pedicle screw 39 and the lower pedicle screw 41 are also fixedly connected by the transverse connecting device.

Figure 59:
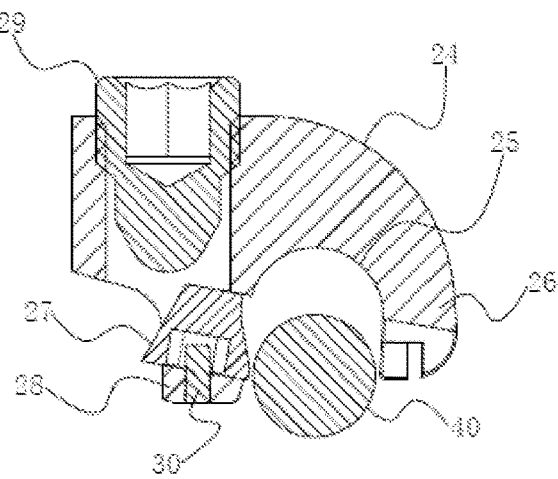
FIG. 59 is a diagram showing a relative positional relationship between a clamping groove of a clamping head and a fixing rod according to an embodiment of the present disclosure.
Figure 60:
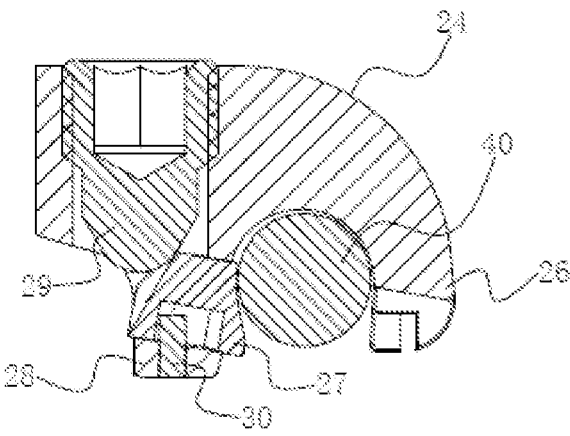
FIG. 60 is a diagram showing a relative positional relationship between a clamping groove of a clamping head and a fixing rod according to an embodiment of the present disclosure.

As shown in FIG. 59 and FIG. 60, when the clamping head 24 of the transverse connection device clamps the fixing rod 40 through the clamping groove 25, the screw plug 29 is firstly screwed out of the vertical through hole 31, and then the first sliding block 27 is pushed to slide away from the clamping groove 25. At this time, the clamping groove 25 is clamped on the fixing rod 40, the screw plug 29 is screwed into the vertical through hole 31, and the screw plug 29 pushes the first sliding block 27 to slide toward the clamping groove 25 until the end face 38 (which is close to the clamping groove 25) of the first sliding block 27 abuts against the fixing rod 40. At this time, the clamping head 24 of the transverse connecting device clamps the fixing rod 40 through the clamping groove 25, that is, the transverse connecting device is fixedly connected with the fixing rod 40.

As shown in FIG. 22 and in combination with FIG. 23 to FIG. 55, the vertebral body distraction support pin includes a pin body and a pin cap. The pin body includes an inner core 13, an outer sleeve 6 and an expansion balloon 10. The inner core 13 is screwed into the outer sleeve 6, and an upper end 14 and a lower end of the inner core 13 extend out of the outer sleeve 6. The lower end of the inner core 13 is provided with a tapered pin head 11, the expansion balloon 10 is sleeved on the inner core 13 between the tapered pin head 11 and the lower end of the outer sleeve 6, the pin cap includes an upper pin cap 4 and a pressurizing cap 12, the upper pin cap 4 has a cylindrical structure, a lower end of a barrel cavity of the upper pin cap 4 is connected to an upper end 16 of the outer sleeve 6, an upper end 14 of the inner core 13 extends to an upper end of the barrel cavity of the upper pin cap 4, and the upper end 14 of the inner core 13 is clamped and slidably connected with the pressurizing cap 12. The pressurizing cap 12 is clamped and slidably connected with the upper pin cap 4, and can slide along the axial direction of the inner core 13 and the upper pin cap 4. When the pressurizing cap 12 slides upward along the axial direction of the upper pin cap 4 to release a clamping sliding connection with the upper pin cap 4, the pressurizing cap 12 still keeps the clamping sliding connection with the inner core 13, and when the tapered pin head 11 moves near the lower end of the outer sleeve 6, the expansion balloon 10 expands. The tapered pin head 11 and the expansion balloon 10 in an expanding state are both located in the fractured vertebral body 22, the supporting block 47 is fixedly connected to an outer wall of the outer sleeve 6, and the supporting block 47 is located outside the fractured vertebral body 22.

Figure 50:
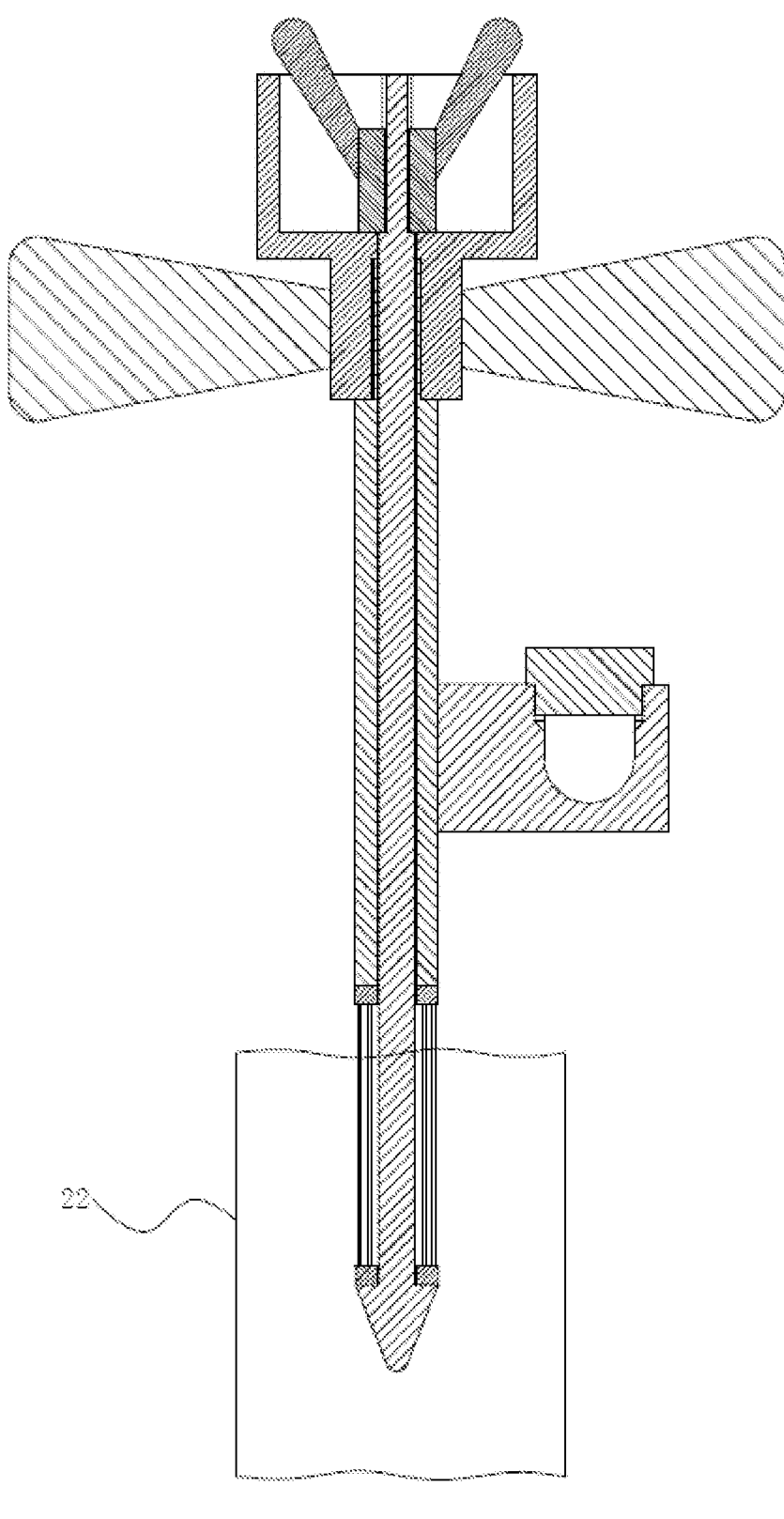
FIG. 50 is a diagram showing a use state of a vertebral body distraction support pin according to an embodiment of the present disclosure.

As shown in FIG. 50 and in combination with FIG. 51 to FIG. 55, when the vertebral body distraction support pin is used, the tapered pin head 11 is aligned with the fractured vertebral body 22, and then the upper pin cap 4 is rotated to screw the lower end of the pin body into the fractured vertebral body 22. During this process, the pin body and the pin cap rotate as a whole, that is, there is no relative rotation between the pin body and the pin cap, among the parts of the pin body and among the parts of the pin cap. Then, the pressurizing cap 12 is slid upward along the axial direction of the upper pin cap 4, so that the clamping sliding connection between the pressurizing cap 12 and the upper pin cap 4 is released. At this time, the pressurizing cap 12 still keeps the clamping sliding connection with the inner core 13, and then the upper pin cap 4 and the outer sleeve 6 are kept stationary. When the pressurizing cap 12 is rotated, the pressurizing cap 12 drives the inner core 13 to rotate. Since the inner core 13 and the outer sleeve 6 are screwed, the inner core 13 can move upward relative to the outer sleeve 6. Further, the tapered pin head 11 moves upward close to the lower end of the outer sleeve 6, and the expansion balloon 10 expands, so that the expansion balloon 10 in the expanding state can support a collapsed bone of the fractured vertebral body 22, and then the outer sleeve 6 and the inner core 13 outside the fractured vertebral body 22 are cut off. It can be seen that the vertebral body distraction support pin can expand the collapsed bone from the inside of the fractured vertebral body 22, so that the fractured vertebral body 22 can be well reduced and the occurrence of long-term complications can be reduced. During the use of the vertebral body distraction support pin, since the supporting block 47 is fixedly connected to the outer wall of the outer sleeve 6, the supporting block 47 moves together with the outer sleeve 6.

As shown in FIG. 22 and in combination with FIG. 23, FIG. 29 to FIG. 32, FIG. 50, FIG. 51 and FIG. 55, the expansion balloon 10 includes an upper collar 7 and a lower collar 9, both of which are sleeved on the inner core 13 between the tapered pin head 11 and the lower end of the outer sleeve 6. The upper collar 7 abuts against the lower end of the outer sleeve 6, and the lower collar 9 abuts against the upper end of the tapered pin head 11, and a plurality of expansion pieces 8 are fixedly connected between the upper collar 7 and the lower collar 9, and the expansion pieces 8 are circumferentially arranged along the inner core 13. When the tapered pin head 11 moves close to the lower end of the outer sleeve 6, the expansion pieces 8 can bulge and deform away from the inner core 13, that is, expand.

As shown in FIG. 22 and in combination with FIG. 23 and FIG. 33 to FIG. 41, the upper pin cap 4 is fixedly connected with two first lugs 5, and the pressurizing cap 12 is fixedly connected with two second lugs 1. The two first lugs 5 are fixedly connected to opposite sides of the upper pin cap 4, and the two second lugs 1 are fixedly connected to opposite sides of the pressurizing cap 12. By providing the lugs, the upper pin cap 4 and the pressurizing cap 12 can be conveniently rotated.

Figures 25, 26, 27, 28:
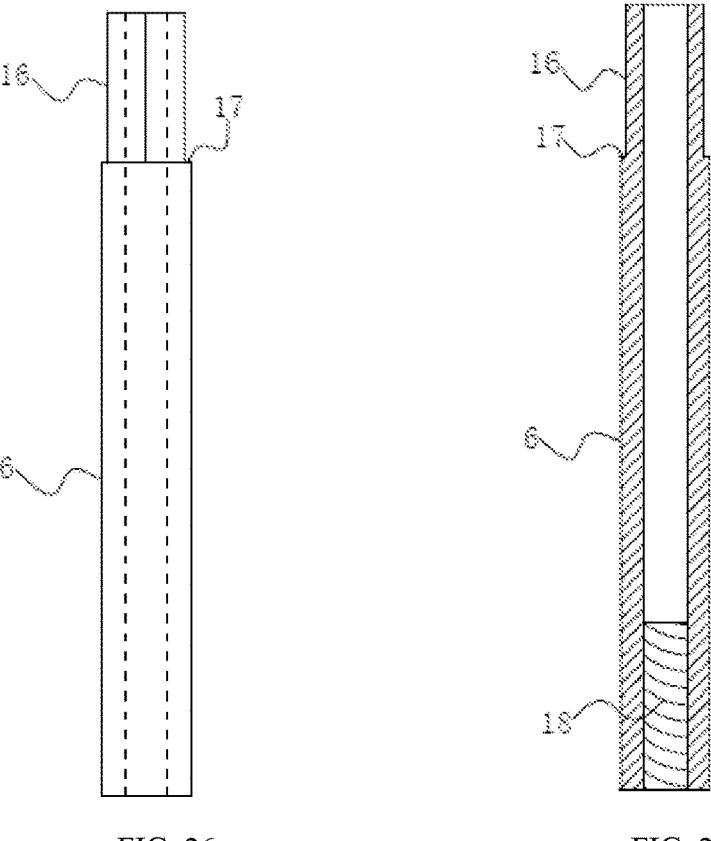
FIG. 25 is a top view of FIG. 24.
FIG. 26 is a front view showing an outer sleeve according to an embodiment of the present disclosure.
FIG. 27 is a front sectional view showing an outer sleeve according to an embodiment of the present disclosure.
FIG. 28 is a top view of FIG. 26.
Figure 29:
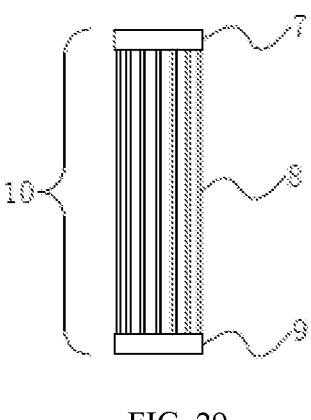
FIG. 29 is a front view showing an expansion balloon (which is in a contracting state) according to an embodiment of the present disclosure.
Figure 30:
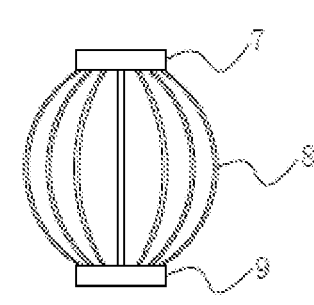
FIG. 30 is a front view showing an expansion balloon (which is in an expanding state) according to an embodiment of the present disclosure.
Figure 31:
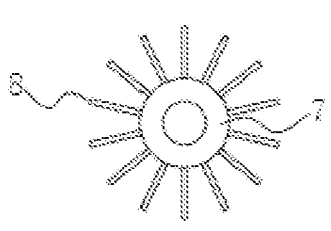
FIG. 31 is a top view of FIG. 30.
Figure 32:
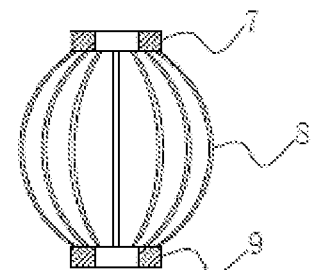
FIG. 32 is a front sectional view showing an expansion balloon (which is in an expanding state) according to an embodiment of the present disclosure.
Figure 33:
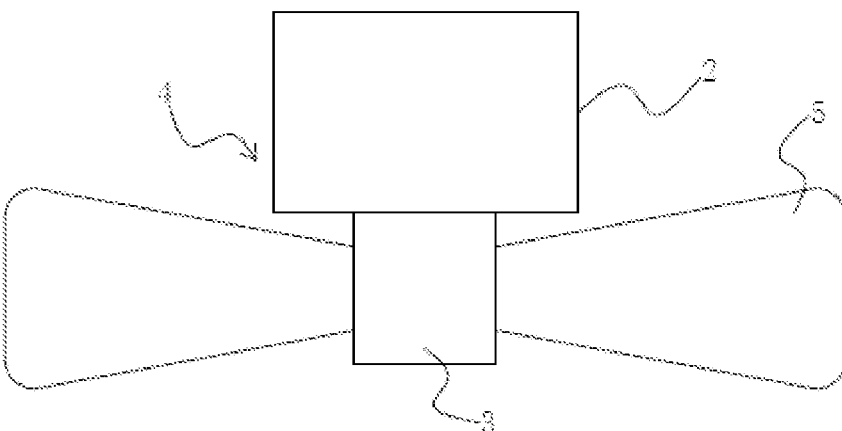
FIG. 33 is a front view showing an upper screw cap according to an embodiment of the present disclosure.
Figure 34:
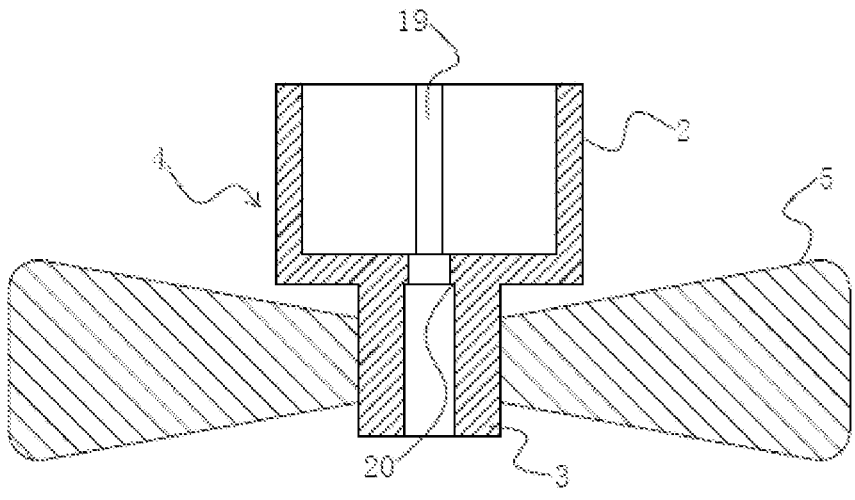
FIG. 34 is a front sectional view showing an upper screw cap according to an embodiment of the present disclosure.
Figure 35:
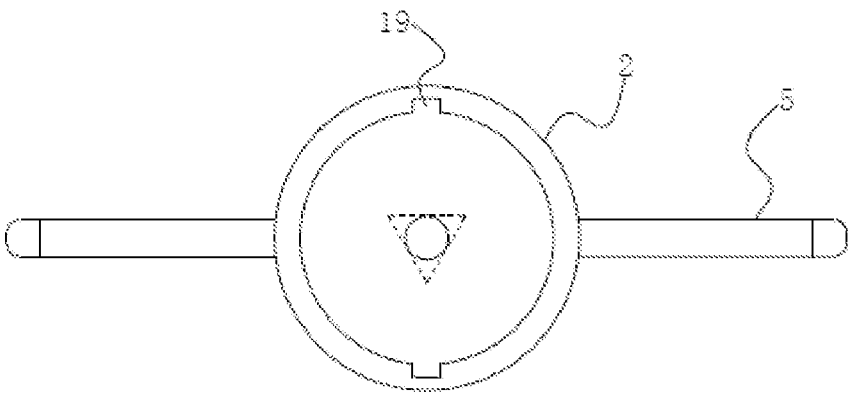
FIG. 35 is a top view showing an upper screw cap according to an embodiment of the present disclosure.
Figure 36:
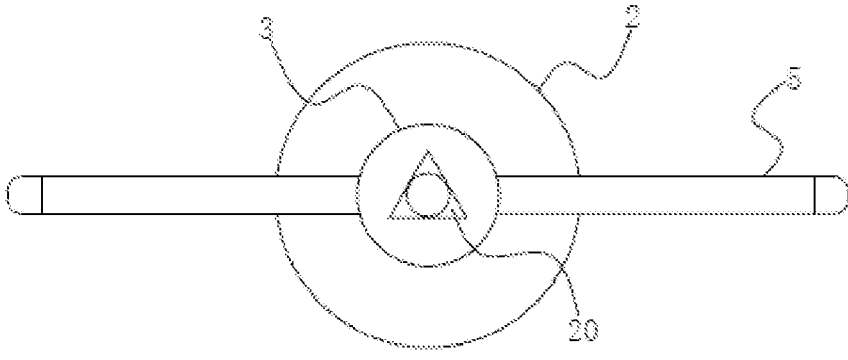
FIG. 36 is a bottom view showing an upper screw cap according to an embodiment of the present disclosure.
Figure 37:
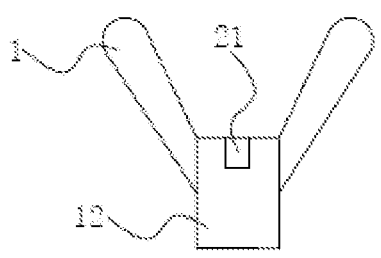
FIG. 37 is a front view showing a pressurizing cap according to an embodiment of the present disclosure.
Figure 38:
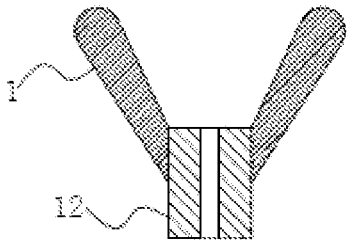
FIG. 38 is a front sectional view showing a pressurizing cap according to an embodiment of the present disclosure.
Figure 39:
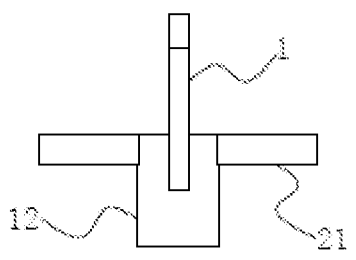
FIG. 39 is a left side view (and also a right side view) showing a pressurizing cap according to an embodiment of the present disclosure.
Figure 40:
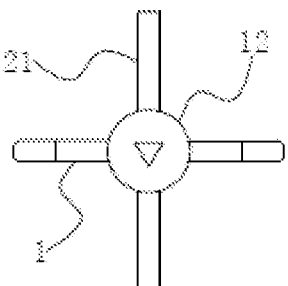
FIG. 40 is a top view showing a pressurizing cap according to an embodiment of the present disclosure.
Figure 41:
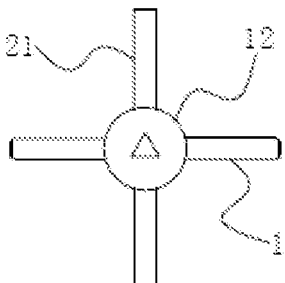
FIG. 41 is a bottom view showing a pressurizing cap according to an embodiment of the present disclosure.

As shown in FIG. 22 and in combination with FIG. 23 and FIG. 33 to FIG. 36, the upper pin cap 4 includes an upper barrel 2 and a lower barrel 3 which are integrally formed. An inner barrel diameter of the upper barrel 2 is larger than that of the lower barrel 3, and an outer barrel diameter of the upper barrel 2 is also larger than that of the lower barrel 3. The two first lugs 5 are fixedly connected to the opposite sides of the lower barrel 3. As shown in FIG. 26 to FIG. 28, the upper end 16 of the outer sleeve 6 has a hollow prism structure, a lower part of a barrel cavity of the lower barrel 3 has a prism shape matched with the upper end 16 of the outer sleeve 6, an upper part of the barrel cavity of the lower barrel 3 is provided with a first clamping table 20, the lower part of the barrel cavity of the lower barrel 3 is sleeved on the upper end 16 of the outer sleeve 6, the upper end 16 of the outer sleeve 6 abuts against the first clamping table 20, and the upper end 14 of the inner core 13 passes through the barrel cavity of the lower barrel 3 and extends into the barrel cavity of the upper barrel 2.

In the embodiment of the present disclosure, the upper end 16 of the outer sleeve 6 has a hollow triangular prism structure, and the lower part of the barrel cavity of the lower barrel 3 is also triangular prism-shaped. As for the first clamping table 20, it is formed in the following way: the upper part of the barrel cavity of the lower barrel 3 is cylindrical, and a diameter of the cylindrical barrel cavity is smaller than that of the lower triangular barrel cavity, so that the first clamping table 20 is formed between the upper part of the barrel cavity of the lower barrel 3 and lower part of the barrel cavity of the lower barrel 3, that is, the above-mentioned first clamping table 20 is formed at the upper part of the barrel cavity of the lower barrel 3.

Figure 46:
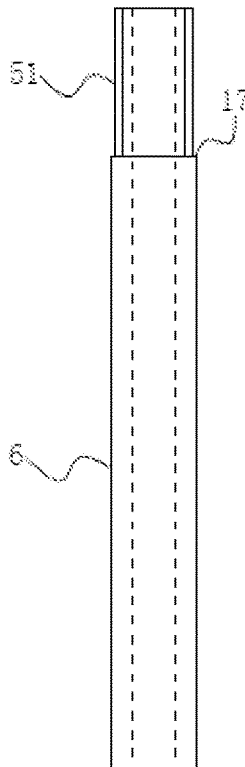
FIG. 46 is a front view showing an outer sleeve according to an embodiment of the present disclosure.
Figure 47:
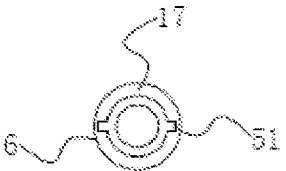
FIG. 47 is a top view of FIG. 46.
Figure 48:
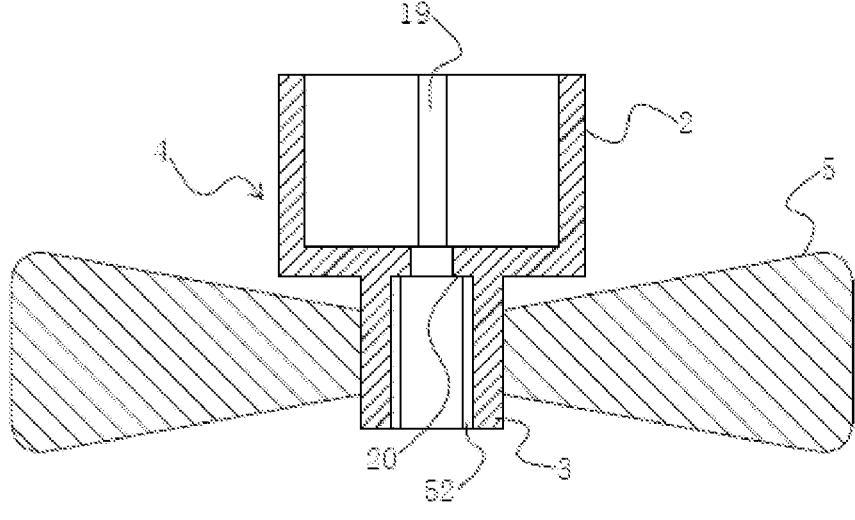
FIG. 48 is a front sectional view showing an upper screw cap according to an embodiment of the present disclosure.
Figure 49:
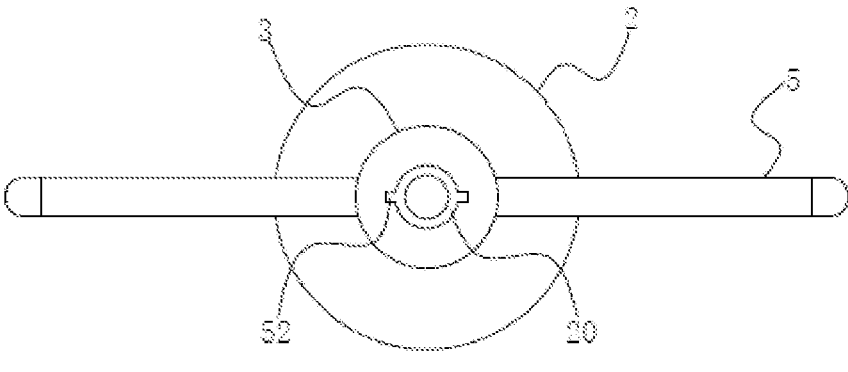
FIG. 49 is a bottom view showing an upper screw cap according to an embodiment of the present disclosure.

In addition to the above-mentioned connection mode between the lower barrel 3 and the outer sleeve 6, it can also be connected in the following ways: as shown in FIG. 46 and in combination with FIG. 47 to FIG. 49, an outer side wall of the upper end 16 of the outer sleeve 6 is provided with a second sliding block 51, and the lower part of the barrel cavity of the lower barrel 3 is provided with a sliding groove 52 axially arranged. After the lower part of the barrel cavity of the lower barrel 3 is sleeved on the upper end 16 of the outer sleeve 6, the second sliding block 51 is located in the sliding groove 52. Certainly, the position of the second sliding block 51 and the position of the sliding groove 52 can also be reversed, that is, the sliding groove 52 is axially arranged on the outer side wall of the upper end 16 of the outer sleeve 6, and the second sliding block 51 is arranged at the lower part of the cavity of the lower barrel 3, and after the lower part of the barrel cavity of the lower barrel 3 is sleeved on the upper end 16 of the outer sleeve 6, the second sliding block 51 is located in the sliding groove 52.

After the lower part of the barrel cavity of the lower barrel 3 is sleeved on the upper end 16 of the outer sleeve 6, the lower barrel 3 and the upper end 16 of the outer sleeve 6 can be either interference fit or clearance fit, since both fit modes can ensure that the upper pin cap 4 and the outer sleeve 6 rotate together or not, that is, when the upper pin cap 4 rotates, the upper pin cap 4 can drive the outer sleeve 6 to rotate synchronously; and when the upper pin cap 4 does not rotate, the outer sleeve 6 will not rotate.

Figure 23:
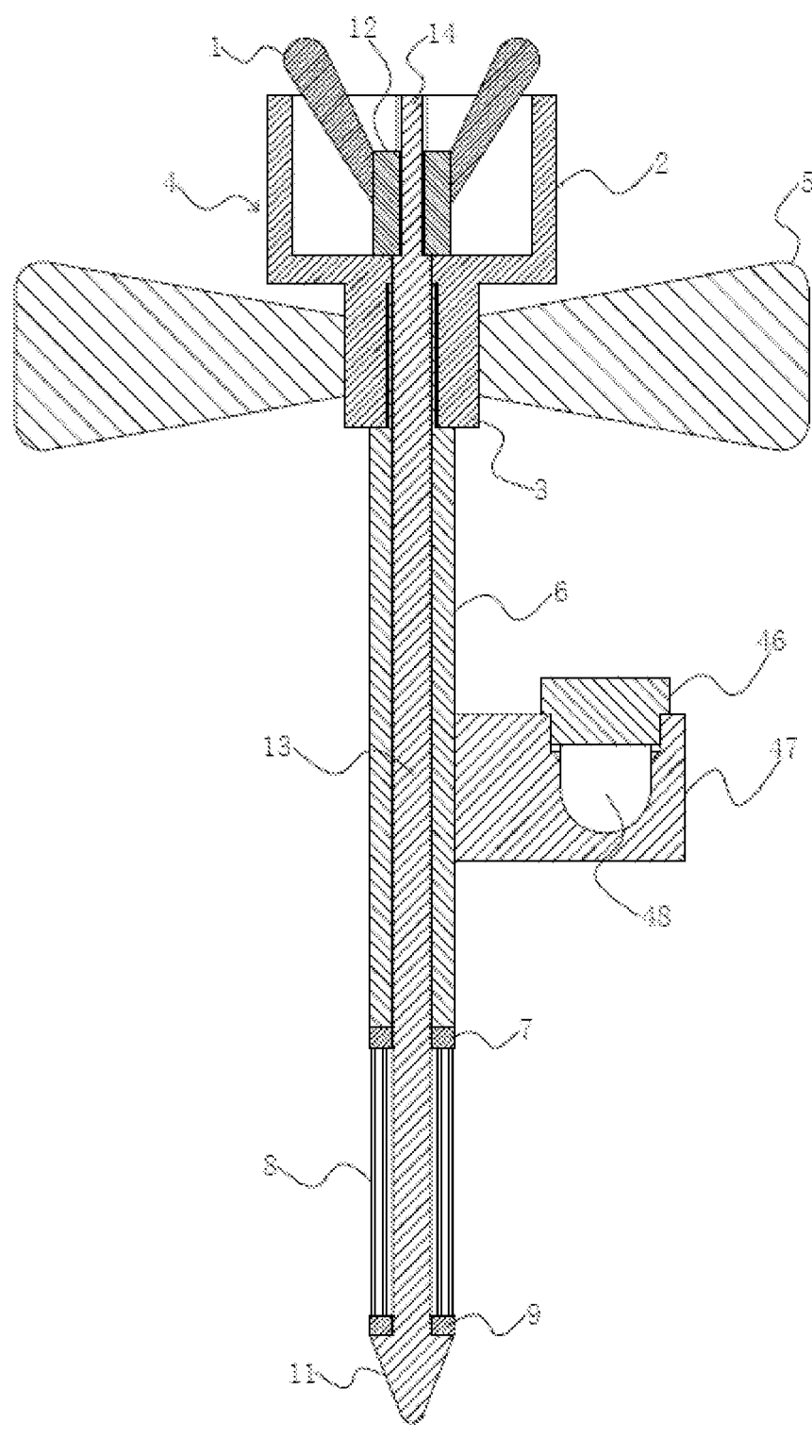
FIG. 23 is a front sectional view showing a vertebral body distraction support pin according to an embodiment of the present disclosure.

As shown in FIG. 23 and in combination with FIG. 26 to FIG. 28, the outer wall of the outer sleeve 6 is provided with a second clamping table 17, and the lower end of the lower barrel 3 abuts against the second clamping table 17, so that the lower barrel 3 and the outer sleeve 6 are more closely matched. The second clamping table 17 is formed in the following way: no matter how the upper end 16 of the outer sleeve 6 is connected with the lower barrel 3, the second clamping table 17 can be formed between the upper end and the lower end as long as the outer diameter of the upper end 16 of the outer sleeve 6 is smaller than the outer diameter of the lower end. Taking FIG. 26 to FIG. 28 as examples, the outer diameters of three sides of the hollow triangular prism structure at the upper end of the outer sleeve 6 are smaller than the outer diameter of the lower end of the outer sleeve 6, and thus the second clamping table 17 is formed between the upper and lower ends of the outer sleeve 6.

As shown in FIG. 23 and in combination with FIG. 24, FIG. 25, FIG. 34, FIG. 35, FIG. 37 to FIG. 41 and FIG. 50 to FIG. 53, the upper end 14 of the inner core 13 has a prismatic structure, and the pressurizing cap 12 has a cylindrical structure. The barrel cavity of the pressurizing cap 12 has a prismatic shape matching with the upper end 14 of the inner core 13. The pressurizing cap 12 is sleeved on the upper end 14 of the inner core 13, and the outer wall of the pressurizing cap 12 is fixedly provided with a second clamping block 21. The inner wall of the upper barrel 2 is provided with a second clamping slot 19 axially arranged, and the second clamping block 21 is positioned in the second clamping slot 19, and can slide along the second clamping slot 19. When the pressurizing cap 12 slides upward along the axial direction of the upper pin cap 4 to make the second clamping block 21 separate from the second clamping slot 19, the pressurizing cap 12 is still sleeved on the upper end 14 of the inner core 13.

In the embodiment of the present disclosure, the upper end 14 of the inner core 13 has a triangular prism structure, and the barrel cavity of the pressurizing cap 12 is triangular prism, so that after the pressurizing cap 12 is sleeved on the upper end 14 of the inner core 13, the clamping sliding connection between the pressurizing cap 12 and the upper end 14 of the inner core 13 is realized, that is, the pressurizing cap 12 can slide up and down along the axial direction of the inner core 13, but the pressurizing cap 12 cannot rotate circumferentially relative to the inner core 13. When the pressurizing cap 12 rotates, the pressurizing cap 12 drives the inner core 13 to rotate synchronously; and when the pressurizing cap 12 does not rotate, the inner core 13 does not rotate.

Figure 51:
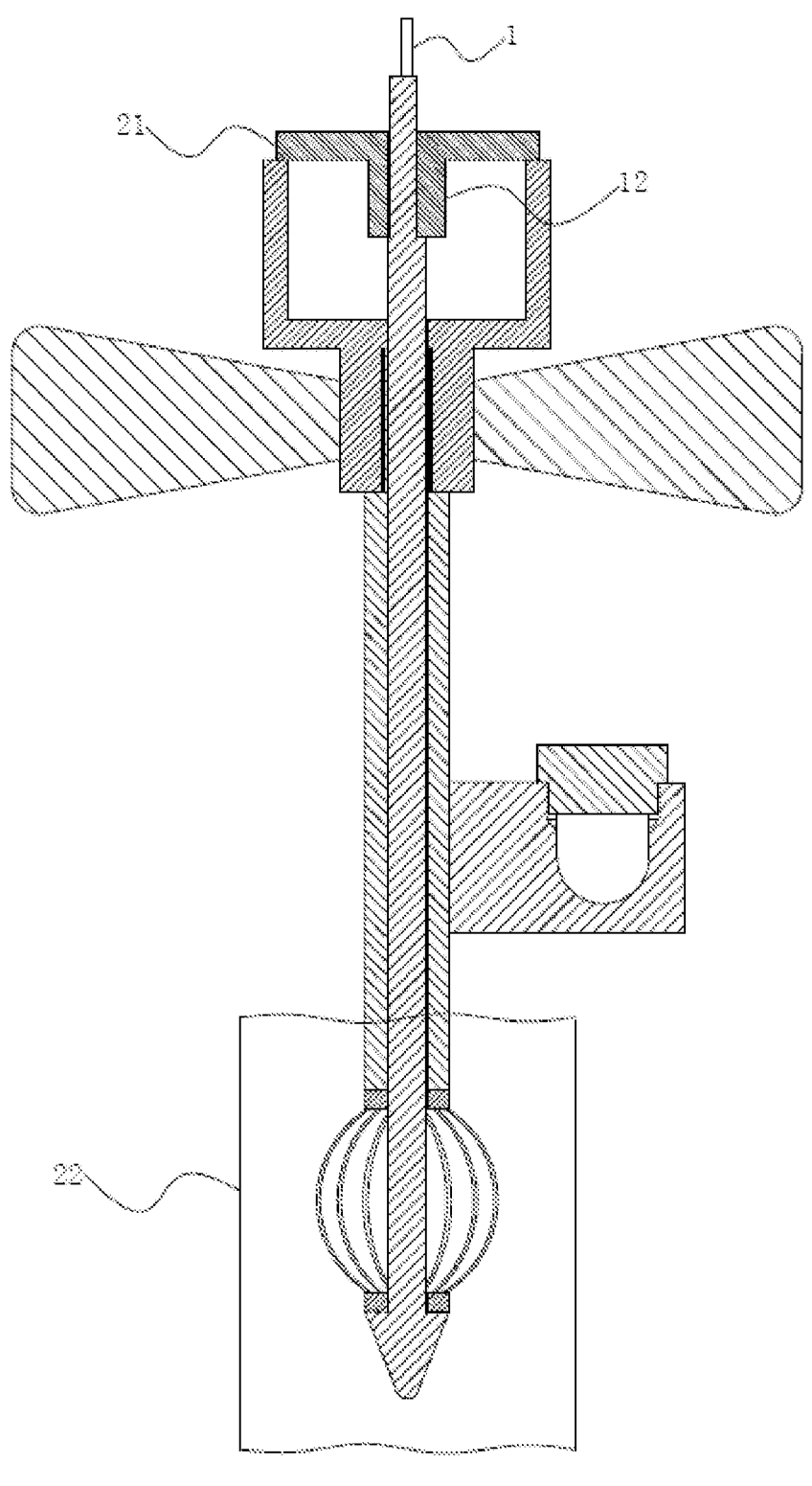
FIG. 51 is a diagram showing a use state of a vertebral body distraction support pin according to an embodiment of the present disclosure.
Figure 52:
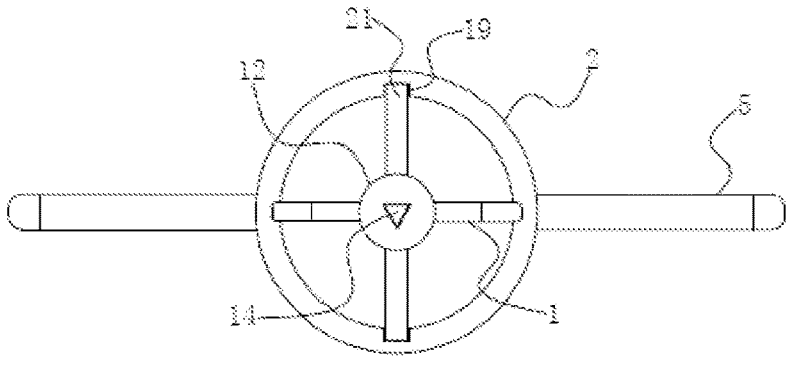
FIG. 52 is a diagram showing a relative positional relationship between a pressurizing cap and an upper screw cap shown in FIG. 50.
Figure 53:
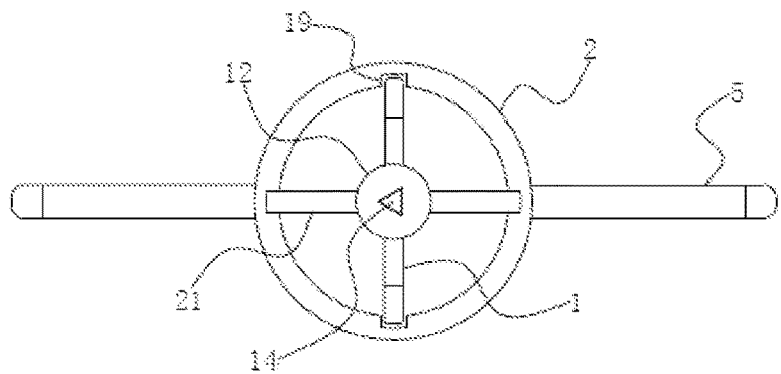
FIG. 53 is a diagram showing a relative positional relationship between a pressurizing cap and an upper screw cap shown in FIG. 51.

The pressurizing cap 12 and the upper pin cap 4 are connected by the second clamping block 21 and the second clamping slot 19, that is, the pressurizing cap 12 can slide up and down along the axial direction of the upper pin cap 4. At this time, the second clamping block 21 slides up and down along the second clamping slot 19. However, due to the limiting effect of the second clamping block 21 and the second clamping slot 19, the pressurizing cap 12 cannot rotate circumferentially relative to the upper pin cap 4, but only both of the pressurizing cap 12 and the upper pin cap 4. When the pressurizing cap 12 slides upward along the axial direction of the upper pin cap 4 and the second clamping block 21 is separated from the second clamping slot 19, the clamping sliding connection between the pressurizing cap 12 and the upper pin cap 4 is released. At this time, the pressurizing cap 12 is still sleeved on the upper end 14 of the inner core 13, that is, the clamping sliding connection between the pressurizing cap 12 and the upper end 14 of the inner core 13 is still maintained. At this time, when the pressurizing cap 12 is rotated, the pressurizing cap 12 can drive the inner core 13 to rotate together with the upper pin cap 4. To facilitate the operation, when the pressurizing cap 12 is rotated, the second clamping block 21 can slide against the upper end face of the upper barrel 2 (as shown in FIG. 51). Since the upper pin cap 4 and the outer sleeve 6 keep synchronous rotation or non-rotation, and the inner core 13 and the outer sleeve 6 are in threaded connection, when the pressurizing cap 12 drives the inner core 13 to rotate relative to the upper pin cap 4, the inner core 13 also rotates relative to the outer sleeve 6, so that the inner core 13 can move upward relative to the outer sleeve 6, and the tapered pin head 11 at the lower end of the inner core 13 moves close to the lower end of the outer sleeve 6. The upper collar 7 and the lower collar 9 of the expansion balloon 10 are squeezed to make the two collars move closer to each other, so that the expansion pieces 8 bulge and deform in the direction away from the inner core 13, that is, in the expanding state, as shown in FIG. 51.

Figure 24:
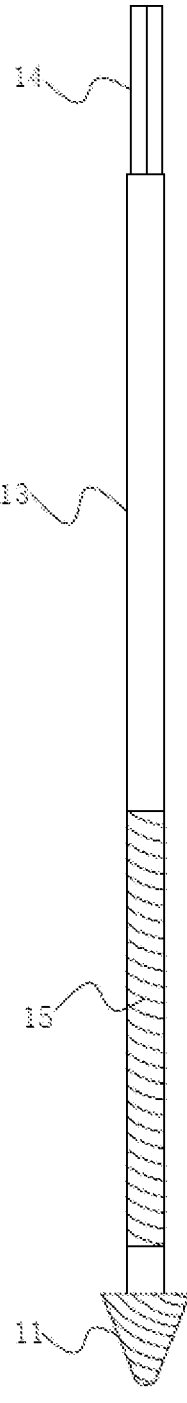
FIG. 24 is a front view showing an inner core according to an embodiment of the present disclosure.

As shown in FIG. 22 and in combination with FIG. 23, FIG. 24 and FIG. 27, an outer side wall of the tapered pin head 11 is provided with screwing threads, so that the tapered pin head 11 can be conveniently screwed into the fractured vertebral body 22. An outer wall of a core between the two ends of the inner core 13 is also provided with an external thread 15, an inner wall of the outer sleeve 6 is provided with an internal thread 18, and the inner core 13 and the outer sleeve 6 are connected by the external thread 15 and the internal thread 18. When the inner core 13 is rotated relative to the outer sleeve 6, the inner core 13 can move up or down relative to the outer sleeve 6. In the embodiment of the present disclosure, in order to make the tapered pin head 11 move close to the lower end of the outer sleeve 6, the expansion balloon 10 needs to be in the expanding state, and the inner core 13 can only move up relative to the outer sleeve 6.

Figures 42, 43:
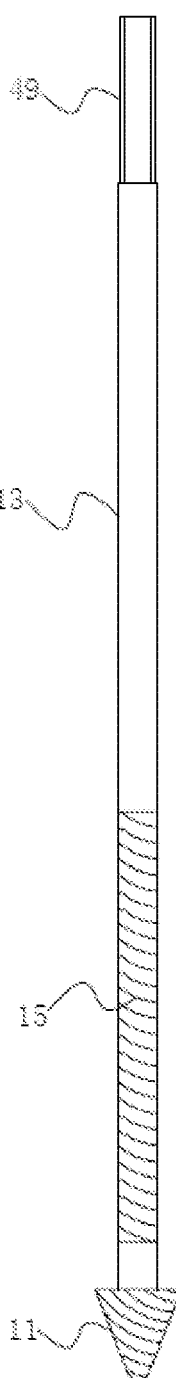
FIG. 42 is a front view showing an inner core according to an embodiment of the present disclosure.
FIG. 43 is a top view of FIG. 42.
Figure 44:
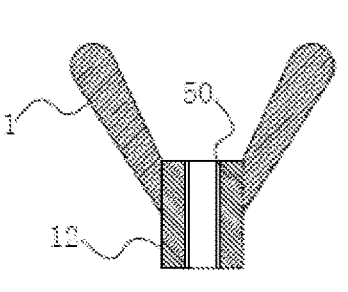
FIG. 44 is a front sectional view showing a pressurizing cap according to an embodiment of the present disclosure.
Figure 45:
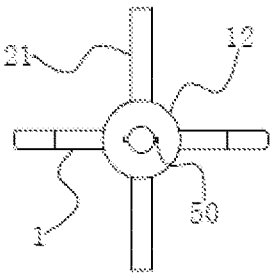
FIG. 45 is a top view showing a pressurizing cap according to an embodiment of the present disclosure.

Certainly, the clamping sliding connection between the pressurizing cap 12 and the upper end of the inner core 13 can also be realized in the following ways: as shown in FIG. 42 and in conjunction with FIG. 43 to FIG. 45, an outer side wall of the upper end 14 of the inner core 13 is provided with a projection 49 axially arranged, and the barrel cavity of the pressurizing cap 12 is provided with a groove 50 axially arranged. When the pressurizing cap 12 is sleeved on the upper end 14 of the inner core 13, the projection 49 is located in the groove 50, and the projection 49 can slide along the groove 50. When the pressurizing cap 12 slides upward along the axial direction of the upper pin cap 4 to make the second clamping block 21 separate from the second clamping slot 19, the pressurizing cap 12 is still sleeved on the upper end 14 of the inner core 13, and the projection 49 is located in the groove 50. Certainly, the position of the projection 49 and the position of the groove 50 can also be reversed, that is, the outer side wall of the upper end 14 of the inner core 13 is provided with the groove 50 axially arranged, and the barrel cavity of the pressurizing cap 12 is provided with the projection 49 axially arranged. Under the limiting effect of the projection 49 and the groove 50, the pressurizing cap 12 can slide up and down along the axial direction of the inner core 13. During this process, the projection 49 also slides up and down along the groove 50, but the pressurizing cap 12 cannot rotate circumferentially relative to the inner core 13. When the pressurizing cap 12 rotates, the pressurizing cap 12 drives the inner core 13 to rotate synchronously; and when the pressurizing cap 12 does not rotate, the inner core 13 will not rotate.

As shown in FIG. 50 and in combination with FIG. 51 to FIG. 55, when the vertebral body distraction support pin is used, the tapered pin head 11 is aligned with the fractured vertebral body 22, the upper pin cap 4 is rotated by the first lug 5, and the lower end of the pin body is screwed into the fractured vertebral body 22. During this process, the pin body and the pin cap rotate as a whole, that is, there is no relative rotation between the pin body and the pin cap, among the parts of the pin body and among the parts of the pin cap. Then, the pressurizing cap 12 is slid upward along the axial direction of the upper pin cap 4, so that the clamping sliding connection between the pressurizing cap 12 and the upper pin cap 4 is released (that is, the second clamping block 21 is separated from the second clamping slot 19). At this time, the pressurizing cap 12 still keeps the clamping sliding connection with the inner core 13, and then the upper pin cap 4 and the outer sleeve 6 are kept stationary. When rotating the pressurizing cap 12 through the second lug 1, the pressurizing cap 12 drives the inner core 13 to rotate. Since the inner core 13 and the outer sleeve 6 are screwed, the inner core 13 can move upward relative to the outer sleeve 6. Further, the tapered pin head 11 moves upward close to the lower end of the outer sleeve 6, and the expansion balloon 10 expands, so that the expansion balloon 10 in the expanding state can support a collapsed bone of the fractured vertebral body 22, and then the outer sleeve 6 and the inner core 13 outside the fractured vertebral body 22 are cut off. After the reduction operation, the expansion balloon 10, a part of the inner core 13 and a part of the outer sleeve 6 are all left in the fractured vertebral body 22, and will not be taken out. Since the threaded connection between the inner core 13 and the outer sleeve 6 left on the fractured vertebral body 22 is still maintained, the expansion balloon 10 in the fractured vertebral body 22 can always be kept in the expanding state. It can be seen that the vertebral body distraction support pin can expand the collapsed bone from the inside of the fractured vertebral body 22, so that the fractured vertebral body 22 can be well reduced and the occurrence of long-term complications can be reduced.

When the present disclosure is used, the upper pedicle screw 39 and the lower pedicle screw 41 are respectively installed on the upper vertebral body 53 and the lower vertebral body 54 of the fractured vertebral body 22, the vertebral body distraction support pin is installed on the fractured vertebral body 22, and then the clamping head 24 of the transverse connecting device clamps the fixing rod 40 through the clamping groove 25, and the connecting rod 23 of the transverse connecting device is fixedly connected to the vertebral body distraction support pin. In this way, the inside of the fractured vertebral body 22 is propped up by the vertebral body distraction support pins, that is, the collapsed bone pieces of the fractured vertebral body 22 are propped up, then the fractured vertebral body 22 is pulled and reduced by the upper pedicle screw 39, the lower pedicle screw 41 and the fixing rod 40, and finally the vertebral body distraction support pins, the fixing rod 40, the upper pedicle screw 39 and the lower pedicle screw 41 are fixedly connected together by the transverse connecting device, thereby realizing the effective reduction of the fractured vertebral body 22 and sufficient anterior support, and ensuring the stability of the spine. It can be seen that the present disclosure can realize the internal expansion and compression of the spine after the screw placement of the injured vertebra, so that the vertebral body can be better restored, and the anterior approach can be supported, thereby greatly avoiding the occurrence of long-term internal fixation failure. Meanwhile, the expansion balloon 10, the inner core 13 and the outer sleeve 6 are all made of titanium alloy or tantalum metal, which has better compatibility with bones, thereby realizing better bone healing and bone ingrowth.

Second Embodiment

Figure 61:
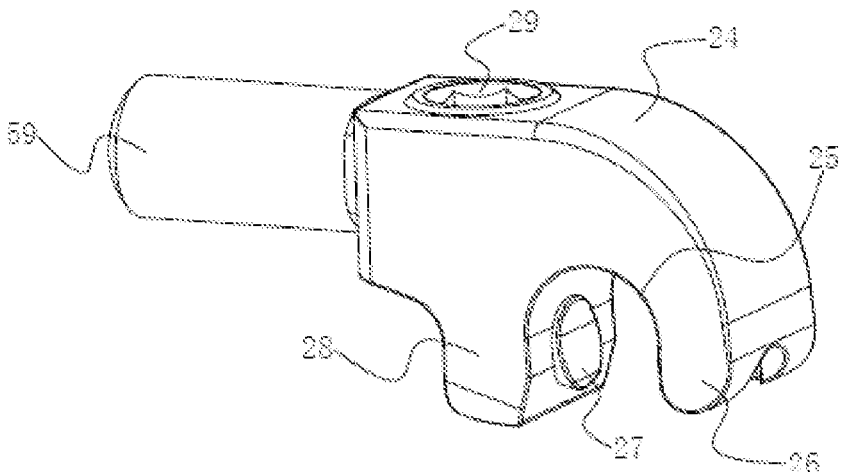
FIG. 61 is a structural schematic diagram showing a transverse connecting device according to an embodiment of the present disclosure.
Figure 62:
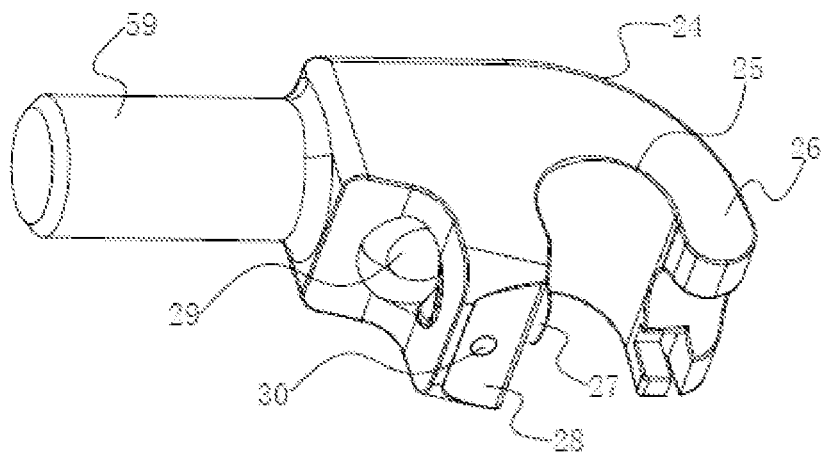
FIG. 62 is a structural schematic diagram showing a transverse connecting device according to an embodiment of the present disclosure.
Figure 63:
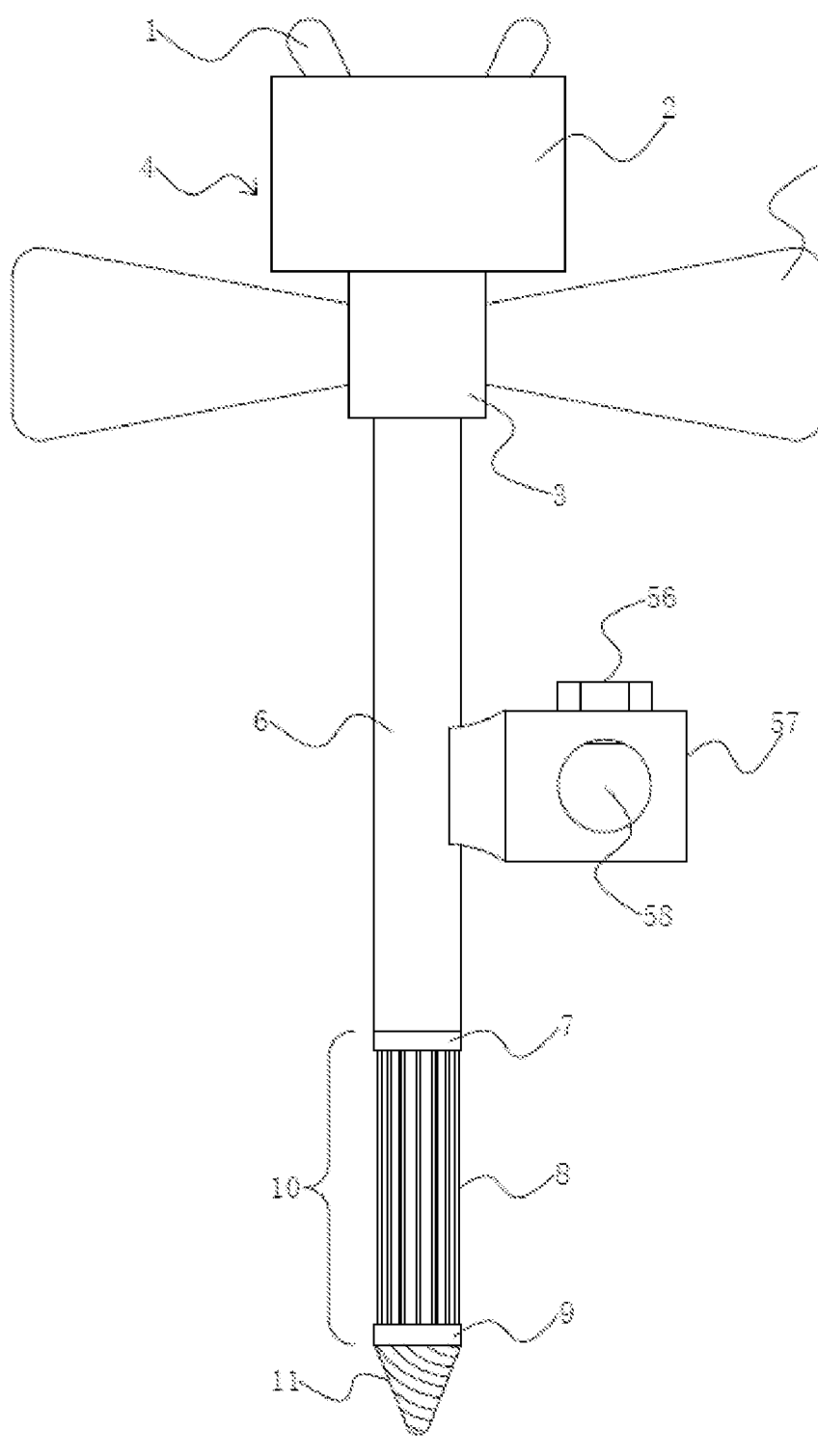
FIG. 63 is a front view showing a vertebral body distraction support pin according to an embodiment of the present disclosure.
Figure 64:
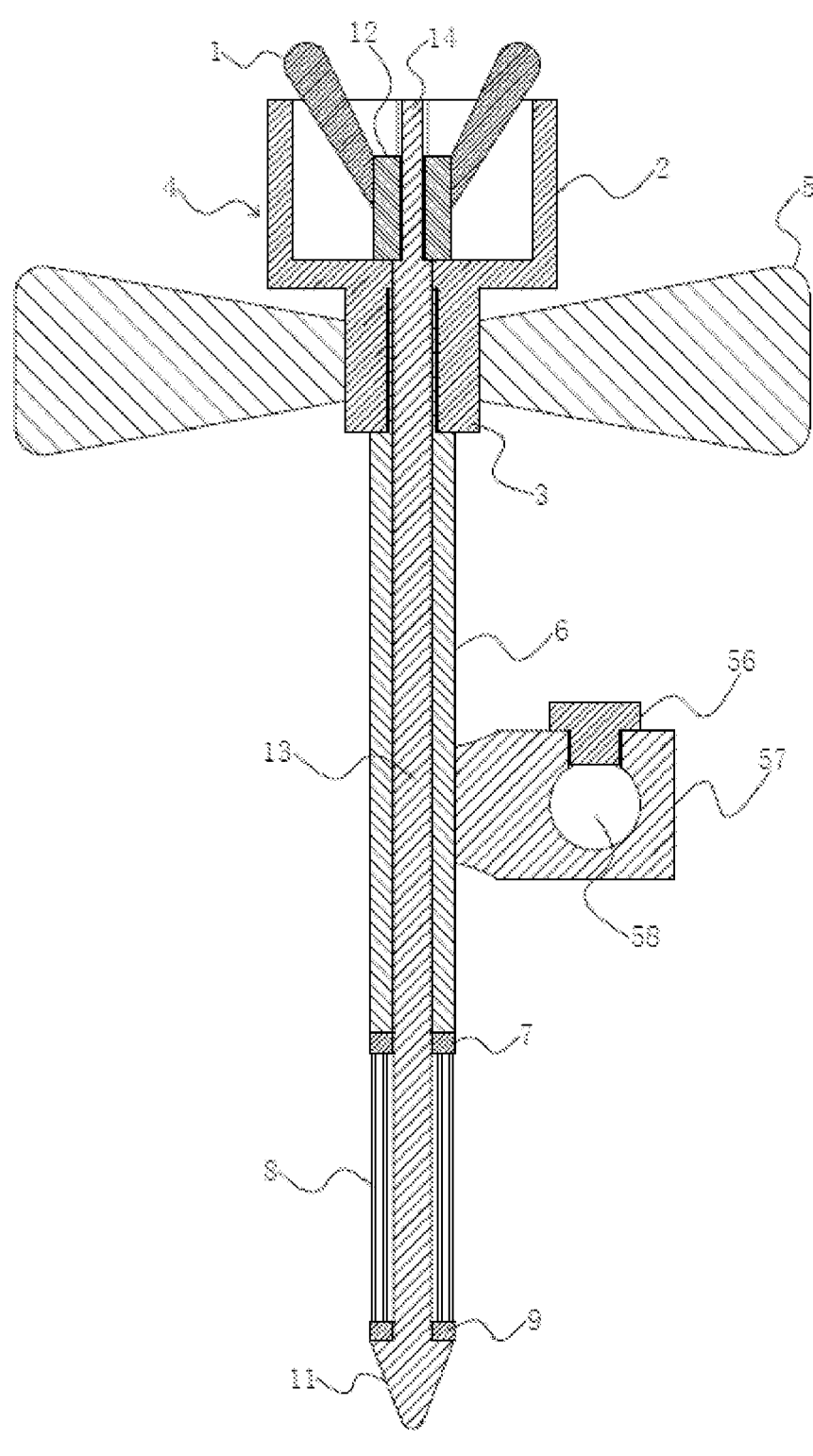
FIG. 64 is a front sectional view showing a vertebral body distraction support pin according to an embodiment of the present disclosure.
Figure 65:
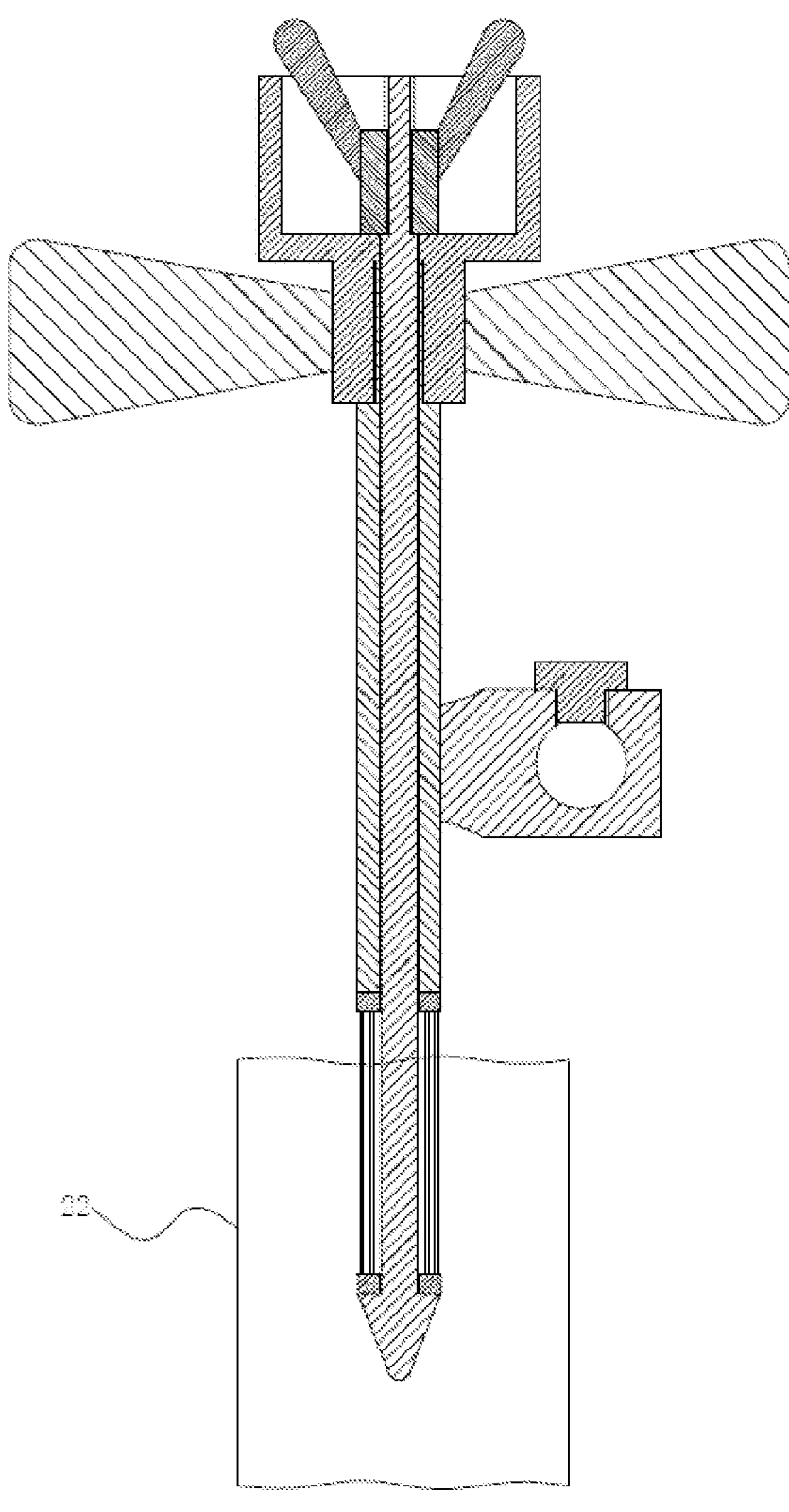
FIG. 65 is a diagram showing a use state of a vertebral body distraction support pin according to an embodiment of the present disclosure.
Figure 66:
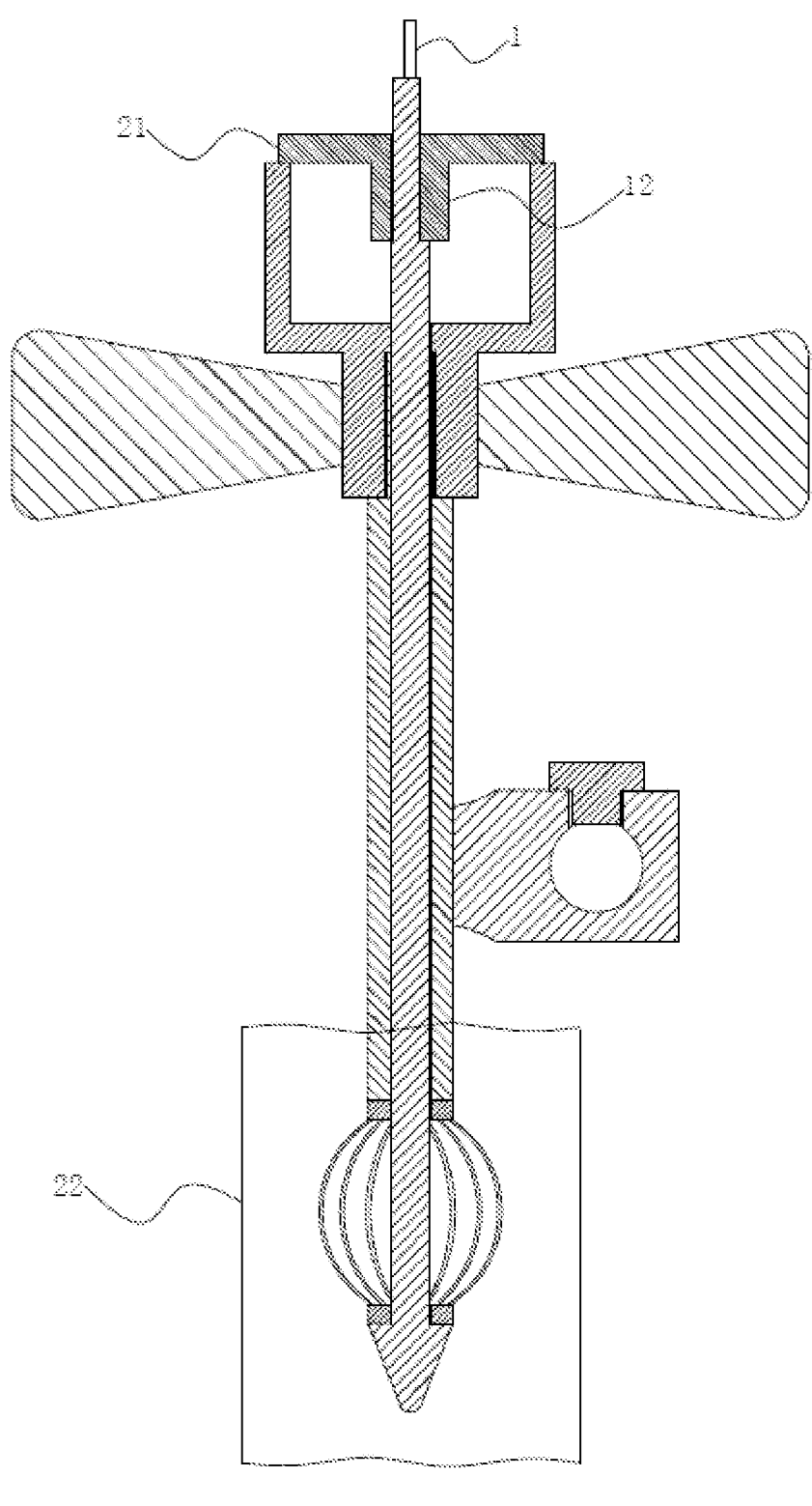
FIG. 66 is a diagram showing a use state of a vertebral body distraction support pin according to an embodiment of the present disclosure.
Figure 67:
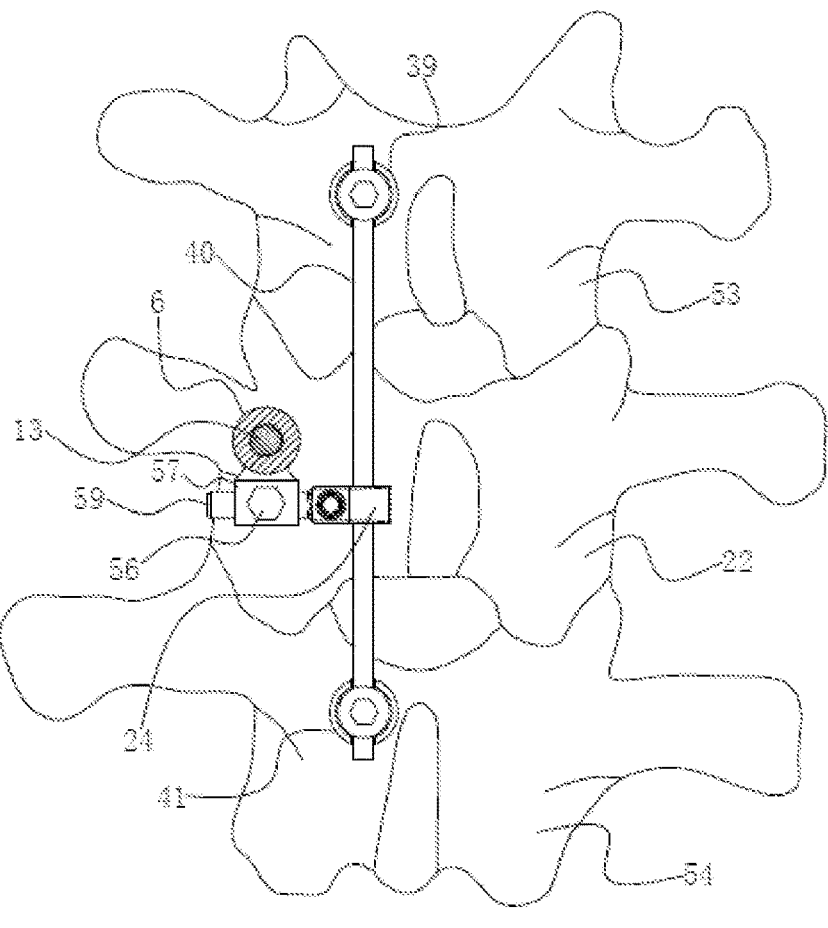
FIG. 67 a diagram showing a use state of a reduction and fixation system according to an embodiment of the present disclosure.
Figure 68:
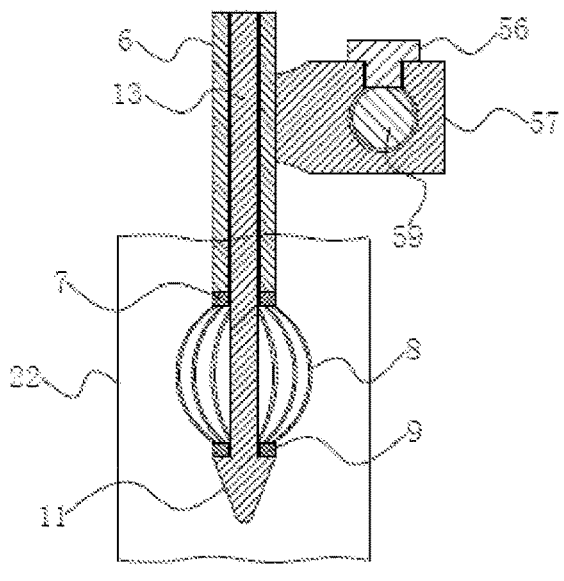
FIG. 68 is a diagram showing a connection state of a supporting block and a connecting rod according to an embodiment of the present disclosure.
Figure 69:
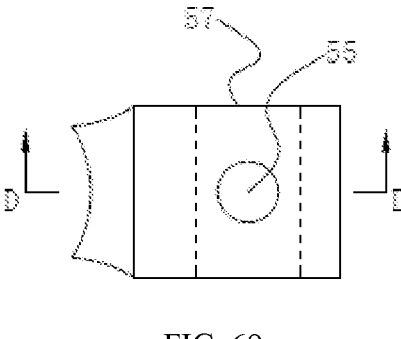
FIG. 69 is a top view showing a supporting block according to an embodiment of the present disclosure.
Figure 70:
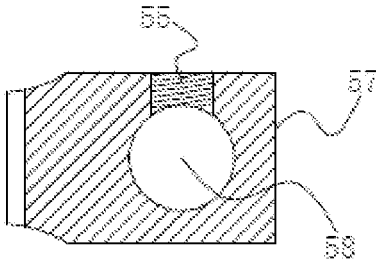
FIG. 70 is a sectional view along line D-D in FIG. 69.
Figure 71:
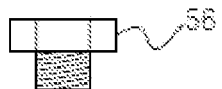
FIG. 71 is a structural schematic diagram showing a screw according to an embodiment of the present disclosure.

As shown in FIG. 61 and in combination with FIG. 62 to FIG. 71, this embodiment differs from the first embodiment in that:

a connecting rod 59 of the transverse connecting device is in a straight line, and one end of the connecting rod 59 is provided with the clamping head 24, and the connecting rod 59 is fixedly connected with the clamping head 24. More specifically, the connecting rod 59 and the clamping head 24 are integrally formed. For the two clamping arms at the lower end of the clamping head 24, the first clamping arm 28 is located between the connecting rod 59 and the second clamping arm 26, and the first clamping arm 28 is provided with the transverse through hole 32.

A supporting block 57 is fixedly connected to the vertebral body distraction support pin. The supporting block 57 is provided with a first through hole 58, and the hole wall of the first through hole 58 is provided with a second through hole 55. The connecting rod 59 of the transverse connecting device is inserted into the first through hole 58, and the second through hole 55 is threaded with a screw 56, which abuts against the connecting rod 59 of the transverse connecting device.

When installing the transverse connecting device, the connecting rod 59 of the transverse connecting device is inserted into the first through hole 58 of the supporting block 57, then the clamping head 24 of the transverse connecting device clamps the fixing rod 40 through the clamping groove 25, and the screw 56 is screwed into the second through hole 55 until the screw 56 abuts against the connecting rod 59 of the transverse connecting device, at which time the screw 56 fixedly connects the connecting rod 59 of the transverse connecting device with the supporting block 57. At the same time, the transverse connecting device also fixedly connects the vertebral body distraction support pin, the fixing rod 40, the upper pedicle screw 39 and the lower pedicle screw 41 together.

In view of above, the difference between this embodiment and the first embodiment is that the structure of the transverse connecting device is different. Specifically, the connecting rod 59 is in the straight line, and only one clamping head 24 is fixedly connected to one end of the connecting rod 59. Certainly, the structure and working principle of the clamping head 24 are completely the same as those of the first embodiment. Since the above differences, the way of fixed connection between the transverse connecting device of this embodiment and the vertebral body distraction support pin is also different from that of the first embodiment (that is, the way of fixed connection between the connecting rod 59 and the supporting block 57 in this embodiment is different from that between the connecting rod 23 and the supporting block 47 in the first embodiment), and the transverse connecting device of this embodiment is fixedly connected with the fixing rod 40 only through one clamping head 24, while the transverse connecting device of the first embodiment is fixedly connected with the fixing rod 40 through two clamping heads 24. Except for the above-mentioned differences, this embodiment is the same as other parts of the first embodiment.

The above-mentioned embodiments only describe the preferred embodiments of the present disclosure, but do not limit the scope of the present disclosure. On the premise of not departing from the design spirit of the present disclosure, all kinds of modifications and improvements made by ordinary technicians in the field to the technical scheme of the present disclosure should fall within the scope of protection determined by the claims of the present disclosure.

INDUSTRIAL APPLICABILITY

The transverse connecting device of the embodiments of the present disclosure includes a connecting rod, wherein the connecting rod is provided with a clamping head, and a lower end of the clamping head is provided with two clamping arms, between which a clamping groove is formed. One clamping arm of the two clamping arms is provided with a transverse through hole, a first sliding block is arranged in the transverse through hole, and the clamping head is provided with a vertical through hole communicating with the transverse through hole. The vertical through hole is internally threaded with a screw plug, and the lower end of the screw plug abuts against the side of the first sliding block far away from the clamping groove. When the screw plug is screwed into the vertical through hole, the screw plug pushes the first sliding block to slide into the clamping groove along the transverse through hole. The reduction and fixation system using the transverse connection device according to the embodiments of the present disclosure further includes a vertebral body distraction support pin, an upper pedicle screw and a lower pedicle screw. The present disclosure can realize the effective reduction of the fractured vertebral body and sufficient anterior support, and ensure the stability of the spine at the same time, and thus, the present disclosure has good application and popularization value, and can be manufactured in batch.

The invention claimed is:

1. A reduction and fixation system using a transverse connecting device, which comprises: a connecting rod provided with clamping heads at two ends respectively, two clamping arms, namely a first clamping arm and a second clamping arm, provided at a lower end of each of clamping heads, a clamping groove formed between the first clamping arm and the second clamping arm, a transverse through hole provided on the first clamping arm or the second clamping arm, a vertical through hole internally threaded with a screw plug, and a first sliding block having a side away from the clamping groove abuts against a lower end of the screw plug, when the screw plug is screwed into the vertical through hole, the screw plug pushes the first sliding block to slide into the clamping groove along the transverse through hole, the first sliding block is provided with a first clamping slot, a wall of the transverse through hole is provided with a first clamping block, and the first clamping block is located in the first clamping slot, the reduction and fixation system comprising: a vertebral body distraction support pin, an upper pedicle screw and a lower pedicle screw, wherein the vertebral body distraction support pin is installed on a fractured vertebral body, the upper pedicle screw and the lower pedicle screw are respectively installed on an upper vertebral body and a lower vertebral body of the fractured vertebral body, a fixing rod is connected between the upper pedicle screw and the lower pedicle screw, the clamping heads of the transverse connecting device clamp the fixing rod through the clamping groove, and the connecting rod of the transverse connecting device is fixedly connected to the vertebral body distraction support pin.

2. The reduction and fixation system according to claim 1, wherein a supporting block is fixedly connected to the vertebral body distraction support pin, the supporting block is provided with an installation groove, the connecting rod of the transverse connection device is inserted into the installation groove, a screw is screwed between two groove walls of the installation groove, the screw abuts against the connecting rod of the transverse connecting device, and the screw fixes the connecting rod in the installation groove.

3. The reduction and fixation system according to claim 2, wherein the vertebral body distraction support pin comprises a pin body and a pin cap, the pin body comprises an inner core, an outer sleeve and an expansion balloon, the inner core is screwed into the outer sleeve, an upper end and a lower end of the inner core extend out of the outer sleeve, the lower end of the inner core is provided with a tapered pin head, the expansion balloon is sleeved on the inner core between the tapered pin head and the lower end of the outer sleeve, the pin cap comprises an upper pin cap and a pressurizing cap, the upper pin cap has a cylindrical structure, a lower end of a barrel cavity of the upper pin cap is connected to an upper end of the outer sleeve, an upper end of the inner core extends to an upper end of the barrel cavity of the upper pin cap, and the upper end of the inner core is clamped and slidably connected with the pressurizing cap, the pressurizing cap is clamped and slidably connected with the upper pin cap and can slide along the axial direction of the inner core and the upper pin cap, when the pressurizing cap slides upward along the axial direction of the upper pin cap to release a clamping sliding connection with the upper pin cap, the pressurizing cap still keeps the clamping sliding connection with the inner core, when the tapered pin head moves near the lower end of the outer sleeve, the expansion balloon expands, the tapered pin head and the expansion balloon in an expanding state are both located in the fractured vertebral body, the supporting block is fixedly connected to an outer wall of the outer sleeve, and the supporting block is located outside the fractured vertebral body.

4. The reduction and fixation system according to claim 3, wherein the expansion balloon comprises an upper collar and a lower collar, both of which are sleeved on the inner core between the tapered pin head and the lower end of the outer sleeve, the upper collar abuts against the lower end of the outer sleeve, the lower collar abuts against the upper end of the tapered pin head, a plurality of expansion pieces are fixedly connected between the upper collar and the lower collar, the expansion pieces are circumferentially arranged along the inner core, when the tapered pin head moves close to the lower end of the outer sleeve, the expansion pieces can bulge and deform away from the inner core, the upper pin cap is fixedly connected with two first lugs, and the pressurizing cap is fixedly connected with two second lugs.

5. The reduction and fixation system according to claim 4, wherein the upper pin cap comprises an upper barrel and a lower barrel which are integrally formed, an inner barrel diameter of the upper barrel is larger than an inner barrel diameter of the lower barrel, the upper end of the outer sleeve has a hollow prism structure, a lower part of a barrel cavity of the lower barrel has a prism shape matched with the upper end of the outer sleeve, an upper part of the barrel cavity of the lower barrel is provided with a first clamping table, the lower part of the barrel cavity of the lower barrel is sleeved on the upper end of the outer sleeve, the upper end of the outer sleeve abuts against the first clamping table, and the upper end of the inner core passes through the barrel cavity of the lower barrel and extends into the barrel cavity of the upper barrel.

6. The reduction and fixation system according to claim 5, wherein the outer wall of the outer sleeve is provided with a second clamping table, and the lower end of the lower barrel abuts against the second clamping table.

7. The reduction and fixation system according to claim 6, wherein the upper end of the inner core has a prismatic structure, the pressurizing cap has a cylindrical structure, the barrel cavity of the pressurizing cap has a prismatic shape matching with the upper end of the inner core, the pressurizing cap is sleeved on the upper end of the inner core, the outer wall of the pressurizing cap is fixedly provided with a second clamping block, the inner wall of the upper barrel is provided with a second clamping slot axially arranged, the second clamping block is positioned in the second clamping slot and can slide along the second clamping slot, when the pressurizing cap slides upward along the axial direction of the upper pin cap to make the second clamping block separate from the second clamping slot, and the pressurizing cap is still sleeved on the upper end of the inner core.

8. The reduction and fixation system according to claim 6, wherein an outer side wall of the upper end of the inner core is provided with a projection axially arranged, the barrel cavity of the pressurizing cap is provided with a groove axially arranged, the pressurizing cap is sleeved on the upper end of the inner core, the projection is located in the groove, the projection can slide along the groove, the outer wall of the pressurizing cap is fixedly provided with a second clamping block, the inner wall of the upper barrel is provided with a second clamping slot axially arranged, the second clamping block is positioned in the second clamping slot and can slide along the second clamping slot, when the pressurizing cap slides upward along the axial direction of the upper pin cap to make the second clamping block separate from the second clamping slot, and the pressurizing cap is still sleeved on the upper end of the inner core and the projection is located in the groove; or the outer side wall of the upper end of the inner core is provided with the groove axially arranged, the barrel cavity of the pressurizing cap is provided with the projection axially arranged, the pressurizing cap is sleeved on the upper end of the inner core, the projection is located in the groove, the projection can slide along the groove, the outer wall of the pressurizing cap is fixedly provided with a second clamping block, the inner wall of the upper barrel is provided with a second clamping slot axially arranged, the second clamping block is positioned in the second clamping slot and can slide along the second clamping slot, when the pressurizing cap slides upward along the axial direction of the upper pin cap to make the second clamping block separate from the second clamping slot, and the pressurizing cap is still sleeved on the upper end of the inner core and the projection is located in the groove.

9. A reduction and fixation system using a transverse connecting device, which comprises: a connecting rod provided with clamping heads at two ends respectively, a second clamping arm and a first clamping arm provided at a lower end of each of the clamping heads respectively with the first clamping arm located between the connecting rod and the second clamping arm, a clamping groove formed between the first clamping arm and the second clamping arm, a transverse through hole provided on the first clamping arm, a vertical through hole internally threaded with a screw plug, and a first sliding block having a side away from the clamping groove abuts against a lower end of the screw plug when the screw plug is screwed into the vertical through hole, the screw plug pushes the first sliding block to slide into the clamping groove along the transverse through hole, the first sliding block is provided with a first clamping slot, a wall of the transverse through bole is provided with a first clamping block, and the first clamping block is located in the first clamping slot, the reduction and fixation system comprising: a vertebral body distraction support pin, an upper pedicle screw and a lower pedicle screw, wherein the vertebral body distraction support pin is installed on a fractured vertebral body, the upper pedicle screw and the lower pedicle screw are respectively installed on an upper vertebral body and a lower vertebral body of the fractured vertebral body, a fixing rod is connected between the upper pedicle screw and the lower pedicle screw, the clamping heads of the transverse connecting device clamp the fixing rod through the clamping groove, and the connecting rod of the transverse connecting device is fixedly connected to the vertebral body distraction support pin.

10. The reduction and fixation system according to claim 9, wherein a supporting block is fixedly connected to the vertebral body distraction support pin, the supporting block is provided with a first through hole, the hole wall of the first through hole is provided with a second through hole, the connecting rod of the transverse connecting device is inserted into the first through hole, the second through hole is threaded with a screw, and the screw abuts against the connecting rod of the transverse connecting device.

11. The reduction and fixation system according to claim 10, wherein the vertebral body distraction support pin comprises a pin body and a pin cap, the pin body comprises an inner core, an outer sleeve and an expansion balloon, the inner core is screwed into the outer sleeve, an upper end and a lower end of the inner core extend out of the outer sleeve, the lower end of the inner core is provided with a tapered pin head, the expansion balloon is sleeved on the inner core between the tapered pin head and the lower end of the outer sleeve, the pin cap comprises an upper pin cap and a pressurizing cap, the upper pin cap has a cylindrical structure, a lower end of a barrel cavity of the upper pin cap is connected to an upper end of the outer sleeve, an upper end of the inner core extends to an upper end of the barrel cavity of the upper pin cap, and the upper end of the inner core is clamped and slidably connected with the pressurizing cap, the pressurizing cap is clamped and slidably connected with the upper pin cap and can slide along the axial direction of the inner core and the upper pin cap, when the pressurizing cap slides upward along the axial direction of the upper pin cap to release a clamping sliding connection with the upper pin cap, the pressurizing cap still keeps the clamping sliding connection with the inner core, when the tapered pin head moves near the lower end of the outer sleeve, the expansion balloon expands, the tapered pin head and the expansion balloon in an expanding state are both located in the fractured vertebral body, the supporting block is fixedly connected to an outer wall of the outer sleeve, and the supporting block is located outside the fractured vertebral body.

12. The reduction and fixation system according to claim 11, wherein the expansion balloon comprises an upper collar and a lower collar, both of which are sleeved on the inner core between the tapered pin head and the lower end of the outer sleeve, the upper collar abuts against the lower end of the outer sleeve, the lower collar abuts against the upper end of the tapered pin head, a plurality of expansion pieces are fixedly connected between the upper collar and the lower collar, the expansion pieces are circumferentially arranged along the inner core, when the tapered pin head moves close to the lower end of the outer sleeve, the expansion pieces can bulge and deform away from the inner core, the upper pin cap is fixedly connected with two first lugs, and the pressurizing cap is fixedly connected with two second lugs.

13. The reduction and fixation system according to claim 12, wherein the upper pin cap comprises an upper barrel and a lower barrel which are integrally formed, an inner barrel diameter of the upper barrel is larger than an inner barrel diameter of the lower barrel, the upper end of the outer sleeve has a hollow prism structure, a lower part of a barrel cavity of the lower barrel has a prism shape matched with the upper end of the outer sleeve, an upper part of the barrel cavity of the lower barrel is provided with a first clamping table, the lower part of the barrel cavity of the lower barrel is sleeved on the upper end of the outer sleeve, the upper end of the outer sleeve abuts against the first clamping table, and the upper end of the inner core passes through the barrel cavity of the lower barrel and extends into the barrel cavity of the upper barrel.

14. The reduction and fixation system according to claim 13, wherein the outer wall of the outer sleeve is provided with a second clamping table, and the lower end of the lower barrel abuts against the second clamping table.

15. The reduction and fixation system according to claim 14, wherein the upper end of the inner core has a prismatic structure, the pressurizing cap has a cylindrical structure, the barrel cavity of the pressurizing cap has a prismatic shape matching with the upper end of the inner core, the pressurizing cap is sleeved on the upper end of the inner core, the outer wall of the pressurizing cap is fixedly provided with a second clamping block, the inner wall of the upper barrel is provided with a second clamping slot axially arranged, the second clamping block is positioned in the second clamping slot and can slide along the second clamping slot, when the pressurizing cap slides upward along the axial direction of the upper pin cap to make the second clamping block separate from the second clamping slot, and the pressurizing cap is still sleeved on the upper end of the inner core.

16. The reduction and fixation system according to claim 14, wherein an outer side wall of the upper end of the inner core is provided with a projection axially arranged, the barrel cavity of the pressurizing cap is provided with a groove axially arranged, the pressurizing cap is sleeved on the upper end of the inner core, the projection is located in the groove, the projection can slide along the groove, the outer wall of the pressurizing cap is fixedly provided with a second clamping block, the inner wall of the upper barrel is provided with a second clamping slot axially arranged, the second clamping block is positioned in the second clamping slot and can slide along the second clamping slot, when the pressurizing cap slides upward along the axial direction of the upper pin cap to make the second clamping block separate from the second clamping slot, and the pressurizing cap is still sleeved on the upper end of the inner core and the projection is located in the groove; or the outer side wall of the upper end of the inner core is provided with the groove axially arranged, the barrel cavity of the pressurizing cap is provided with the projection axially arranged, the pressurizing cap is sleeved on the upper end of the inner core, the projection is located in the groove, the projection can slide along the groove, the outer wall of the pressurizing cap is fixedly provided with a second clamping block, the inner wall of the upper barrel is provided with a second clamping slot axially arranged, the second clamping block is positioned in the second clamping slot and can slide along the second clamping slot, when the pressurizing cap slides upward along the axial direction of the upper pin cap to make the second clamping block separate from the second clamping slot, and the pressurizing cap is still sleeved on the upper end of the inner core and the projection is located in the groove.

* * * * *